US010668028B2

(12) United States Patent
Narain et al.

(10) Patent No.: US 10,668,028 B2
(45) Date of Patent: Jun. 2, 2020

(54) METHODS AND USE OF INDUCING APOPTOSIS IN CANCER CELLS

(71) Applicant: Berg LLC, Nashville, TN (US)

(72) Inventors: Niven Rajin Narain, Cambridge, MA (US); Indushekhar Persaud, Homestead, FL (US); John Patrick McCook, Frisco, TX (US)

(73) Assignee: Berg LLC, Framingham, MA (US)

(*) Notice: Subject to any disclaimer, the term of this patent is extended or adjusted under 35 U.S.C. 154(b) by 0 days.

(21) Appl. No.: 14/705,591

(22) Filed: May 6, 2015

(65) Prior Publication Data

US 2015/0231091 A1    Aug. 20, 2015

Related U.S. Application Data

(63) Continuation of application No. 14/177,171, filed on Feb. 10, 2014, now abandoned, which is a continuation of application No. 13/345,570, filed on Jan. 6, 2012, now abandoned, which is a continuation of application No. 12/936,852, filed as application No. PCT/US2009/039992 on Apr. 9, 2009, now abandoned.

(60) Provisional application No. 61/044,085, filed on Apr. 11, 2008.

(51) Int. Cl.
| | | |
|---|---|---|
| *A61K 31/122* | (2006.01) | |
| *C12Q 1/6869* | (2018.01) | |
| *C12Q 1/6809* | (2018.01) | |
| *A61K 9/127* | (2006.01) | |
| *A61K 9/02* | (2006.01) | |
| *A61K 9/00* | (2006.01) | |
| *A61K 9/06* | (2006.01) | |
| *A61K 9/12* | (2006.01) | |

(52) U.S. Cl.
CPC ............ *A61K 31/122* (2013.01); *A61K 9/127* (2013.01); *A61K 9/0014* (2013.01); *A61K 9/0019* (2013.01); *A61K 9/0048* (2013.01); *A61K 9/0075* (2013.01); *A61K 9/02* (2013.01); *A61K 9/06* (2013.01); *A61K 9/12* (2013.01)

(58) Field of Classification Search
None
See application file for complete search history.

(56) References Cited

U.S. PATENT DOCUMENTS

| | | |
|---|---|---|
| 4,452,901 A | 6/1984 | Gordon et al. |
| 4,483,873 A | 11/1984 | Ohashi et al. |
| 4,515,736 A | 5/1985 | Deamer |
| 4,525,350 A | 6/1985 | Casey et al. |
| 4,636,381 A | 1/1987 | Takada et al. |
| 4,654,373 A | 3/1987 | Bertelli |
| 4,824,669 A | 4/1989 | Folkers et al. |
| 4,895,727 A | 1/1990 | Allen |
| 5,015,483 A | 5/1991 | Haynes et al. |
| 5,362,494 A | 11/1994 | Zysman et al. |
| 5,378,461 A | 1/1995 | Neigut |
| 5,527,789 A | 6/1996 | Nyce |
| 5,602,184 A | 2/1997 | Myers et al. |
| 5,603,958 A | 2/1997 | Morein et al. |
| 5,605,930 A | 2/1997 | Samid |
| 5,651,991 A | 7/1997 | Sugiyama et al. |
| 5,700,482 A | 12/1997 | Frederiksen et al. |
| 5,719,303 A | 2/1998 | Yoshida et al. |
| 5,770,222 A | 6/1998 | Unger et al. |
| 5,876,737 A | 3/1999 | Schonrock et al. |
| 5,889,062 A | 3/1999 | Hoppe et al. |
| 5,891,465 A | 4/1999 | Keller et al. |
| 5,912,272 A | 6/1999 | Hoppe et al. |
| 5,944,012 A | 8/1999 | Pera |
| 5,962,243 A | 10/1999 | Brown et al. |
| 6,005,086 A | 12/1999 | Evans et al. |
| 6,048,886 A | 4/2000 | Neigut |
| 6,071,495 A | 6/2000 | Unger et al. |

(Continued)

FOREIGN PATENT DOCUMENTS

| | | |
|---|---|---|
| EP | 0397129 | 11/1990 |
| JP | S57075916 | 5/1982 |

(Continued)

OTHER PUBLICATIONS

Lockwood et al. Partial and Complete Regression of Breast Cancer in Patients in Relation to Dosage of Coenzyme Q10. Mar. 30, 1994. vol. 199, No. 3, pp. 1504-1508.*
Oca et al. Caspase-3 activity, response to chemotherapy and clinical outcome in patients with colon cancer. Published online Sep. 4, 2007. Int. J. Colorectal Dis. vol. 23, pp. 21-27.*
"Fact Sheet: Brain Tumor," Los Angeles Caregiver Resource Center [online], 2004 (retrieved on Jun. 19, 2012 from the internet: <URL : http://lacrc.usc.edu/forms/brain tumor.pdf); p. 1-12.
Bliznakov, E., "Effect of Stimulation of the Host Defense System by Coenzyme Q10 on Dibenzpyrene-Induced Tumors and Infection with Friend Leukemia Virus in Mice", Proc. Nat. Acad. Sci. USA, 70(2): 390-394 (Feb. 1973).

(Continued)

*Primary Examiner* — Channing S Mahatan
(74) *Attorney, Agent, or Firm* — McCarter & English, LLP; Jill Mello

(57) ABSTRACT

The present disclosure relates to a method of inducing apoptosis in a cancer cell by delivery of exogenous Coenzyme Q1O or its metabolites thereof in a pharmaceutically acceptable carrier to effectuate cell contact of endogenous Coenzyme Q1O or its metabolites thereof in addition to but not limited to mevalonic acid and oleic acid to form an intracellular complex. The present disclosure also provides a method of modulating the p53 pathway and Bcl-2 protein family in a manner that restores the apoptotic potential to a cancer cell by delivery of Coenzyme Q1O in a pharmaceutically acceptable carrier. The present disclosure further provides a method to specifically normalize the ratio of pro-apoptotic and anti-apoptotic members of the Bcl-2 gene family in a proportion to re-program a cancer cell to undergo apoptosis.

4 Claims, 16 Drawing Sheets

(56) References Cited

U.S. PATENT DOCUMENTS

| | | |
|---|---|---|
| 6,093,706 A | 7/2000 | Zeligs |
| 6,093,743 A | 7/2000 | Lai et al. |
| 6,184,353 B1 | 2/2001 | Evans et al. |
| 6,228,891 B1 | 5/2001 | Enzmann et al. |
| 6,261,575 B1 | 7/2001 | Hoppe et al. |
| 6,348,506 B2 | 2/2002 | Sneed |
| 6,372,234 B1 | 4/2002 | Deckers et al. |
| 6,416,957 B1 | 7/2002 | Evans et al. |
| 6,417,233 B1 | 7/2002 | Sears et al. |
| 6,441,050 B1 | 8/2002 | Chopra |
| 6,461,593 B1 | 10/2002 | Hanioka et al. |
| 6,465,517 B1 | 10/2002 | Van Der Zee |
| 6,468,552 B1 | 10/2002 | Stahl et al. |
| 6,469,061 B1 | 10/2002 | Flescher et al. |
| 6,482,943 B1 | 11/2002 | Blokhin et al. |
| 6,503,506 B1 | 1/2003 | Germano |
| 6,503,523 B2 | 1/2003 | Hoppe et al. |
| 6,506,915 B1 | 1/2003 | West |
| 6,511,800 B1 | 1/2003 | Singh |
| 6,531,117 B2 | 3/2003 | Heger et al. |
| 6,569,463 B2 | 5/2003 | Patel et al. |
| 6,573,284 B1 | 6/2003 | Riley et al. |
| 6,576,660 B1 | 6/2003 | Liao et al. |
| 6,576,678 B1 | 6/2003 | Bruening et al. |
| 6,582,710 B2 | 6/2003 | Deckers et al. |
| 6,582,723 B2 | 6/2003 | Gorsek |
| 6,596,287 B2 | 7/2003 | Deckers et al. |
| 6,599,513 B2 | 7/2003 | Deckers et al. |
| 6,623,746 B1 | 9/2003 | Wadle et al. |
| 6,630,160 B1 | 10/2003 | Evans et al. |
| 6,632,443 B2 | 10/2003 | Borowy-Borowski et al. |
| 6,652,891 B2 | 11/2003 | Selzer |
| 6,682,763 B2 | 1/2004 | Kuno et al. |
| 6,686,485 B2 | 2/2004 | West |
| 6,696,484 B2 | 2/2004 | Liao et al. |
| 6,726,924 B2 | 4/2004 | Keller |
| 6,727,234 B2 | 4/2004 | Wiemer et al. |
| 6,733,790 B1 | 5/2004 | Garces Garces |
| 6,753,325 B2 | 6/2004 | Rosenbloom |
| 6,803,193 B1 | 10/2004 | Hopper et al. |
| 6,806,069 B2 | 10/2004 | Chokshi |
| 6,809,176 B2 | 10/2004 | Blokhin et al. |
| 6,866,864 B2 | 3/2005 | Mousa |
| 6,867,024 B2 | 3/2005 | Chokshi |
| 6,906,106 B2 | 6/2005 | Chevalier |
| 6,923,988 B2 | 8/2005 | Patel et al. |
| 7,005,274 B1 | 2/2006 | Terkeltaub et al. |
| 7,060,733 B2 | 6/2006 | Pandol et al. |
| 7,083,572 B2 | 8/2006 | Unger et al. |
| 7,083,780 B2 | 8/2006 | Ansmann et al. |
| 7,091,241 B2 | 8/2006 | Gilloteaux et al. |
| 7,101,536 B2 | 9/2006 | Mongiat et al. |
| 7,132,268 B2 | 11/2006 | Miyake et al. |
| 7,147,841 B2 | 12/2006 | Herzog |
| 7,169,385 B2 | 1/2007 | Fantuzzi et al. |
| 7,169,590 B2 | 1/2007 | Ueda et al. |
| 7,176,171 B2 | 2/2007 | Nieendick et al. |
| 7,179,880 B2 | 2/2007 | Kawa et al. |
| 7,182,938 B2 | 2/2007 | Andre et al. |
| 7,182,950 B2 | 2/2007 | Garti et al. |
| 7,198,801 B2 | 4/2007 | Carrara et al. |
| 7,208,298 B2 | 4/2007 | Miyake et al. |
| 7,247,714 B2 | 7/2007 | Kunsch et al. |
| 7,250,174 B2 | 7/2007 | Lee et al. |
| 7,268,107 B2 | 9/2007 | Nieendick et al. |
| 7,273,606 B2 | 9/2007 | Fantuzzi et al. |
| 7,279,456 B2 | 10/2007 | Dufay et al. |
| 7,311,897 B2 | 12/2007 | Ehlis et al. |
| 7,318,929 B2 | 1/2008 | Schieferstein et al. |
| 7,357,918 B2 | 4/2008 | Comte et al. |
| 7,456,161 B2 | 11/2008 | Nyce |
| 7,635,722 B1 | 12/2009 | Bachynsky et al. |
| 7,776,894 B2 | 8/2010 | Ronai et al. |
| 7,824,673 B2 | 11/2010 | Wegman et al. |
| 7,858,659 B2 | 12/2010 | Hoffman et al. |
| 7,862,995 B2 | 1/2011 | Bacus et al. |
| 7,879,823 B2 | 2/2011 | Seiberg et al. |
| 7,906,140 B2 | 3/2011 | Bromley et al. |
| 8,147,825 B2 | 4/2012 | Hsia et al. |
| 8,293,227 B2 | 10/2012 | Hsia et al. |
| 8,454,945 B2 | 6/2013 | McCook et al. |
| 8,562,976 B2 | 10/2013 | Hsia et al. |
| 8,586,030 B2 | 11/2013 | Hsia et al. |
| 8,771,680 B2 | 7/2014 | Hsia et al. |
| 2001/0022965 A1 | 9/2001 | Heger et al. |
| 2001/0053356 A1 | 12/2001 | Mousa |
| 2002/0039595 A1 | 4/2002 | Keller |
| 2002/0044913 A1 | 4/2002 | Hamilton |
| 2002/0045230 A1 | 4/2002 | Rosen et al. |
| 2002/0048559 A1 | 4/2002 | Shinoda et al. |
| 2002/0048798 A1 | 4/2002 | Avery et al. |
| 2002/0049253 A1 | 4/2002 | Kaddurah-Daouk |
| 2002/0049422 A1 | 4/2002 | Brewitt |
| 2002/0058712 A1 | 5/2002 | Sneed |
| 2002/0071852 A1 | 6/2002 | Deckers et al. |
| 2002/0091288 A1 | 7/2002 | Wilbur et al. |
| 2002/0106337 A1 | 8/2002 | Deckers et al. |
| 2002/0114820 A1 | 8/2002 | Deckers et al. |
| 2002/0127252 A1 | 9/2002 | Kramer et al. |
| 2002/0136711 A1 | 9/2002 | Cochran |
| 2002/0146463 A1 | 10/2002 | Clayton |
| 2002/0155151 A1 | 10/2002 | Enzmann et al. |
| 2002/0156302 A1 | 10/2002 | West |
| 2002/0164317 A1 | 11/2002 | Gorsek |
| 2002/0182199 A1 | 12/2002 | Hoppe et al. |
| 2002/0198177 A1 | 12/2002 | Horrobin |
| 2003/0012762 A1 | 1/2003 | Zulli et al. |
| 2003/0012779 A1 | 1/2003 | Grieb et al. |
| 2003/0012825 A1 | 1/2003 | Kapper |
| 2003/0031688 A1 | 2/2003 | Ghosh et al. |
| 2003/0044441 A1 | 3/2003 | Schmid et al. |
| 2003/0077297 A1 | 4/2003 | Chen et al. |
| 2003/0087331 A1 | 5/2003 | Pettit et al. |
| 2003/0091518 A1 | 5/2003 | Pauly et al. |
| 2003/0103954 A1 | 6/2003 | Rosenbloom |
| 2003/0104048 A1 | 6/2003 | Patel et al. |
| 2003/0104080 A1 | 6/2003 | Singh et al. |
| 2003/0105027 A1 | 6/2003 | Rosenbloom |
| 2003/0105030 A1 | 6/2003 | Liao et al. |
| 2003/0105031 A1 | 6/2003 | Rosenbloom |
| 2003/0108493 A1 | 6/2003 | Henry et al. |
| 2003/0113354 A1 | 6/2003 | Schmid et al. |
| 2003/0118525 A1 | 6/2003 | Grigg |
| 2003/0118536 A1 | 6/2003 | Rosenbloom |
| 2003/0118576 A1 | 6/2003 | Brancato et al. |
| 2003/0124158 A1 | 7/2003 | Heidenfelder et al. |
| 2003/0129150 A1 | 7/2003 | Pauly et al. |
| 2003/0143166 A1 | 7/2003 | Heger et al. |
| 2003/0144346 A1 | 7/2003 | Liao et al. |
| 2003/0152598 A1 | 8/2003 | Heidenfelder et al. |
| 2003/0161849 A1 | 8/2003 | Heidenfelder et al. |
| 2003/0167556 A1 | 9/2003 | Kelley |
| 2003/0170265 A1 | 9/2003 | Henry et al. |
| 2003/0180231 A1 | 9/2003 | Danoux et al. |
| 2003/0180278 A1 | 9/2003 | Hoppe et al. |
| 2003/0180352 A1 | 9/2003 | Patel et al. |
| 2003/0185865 A1 | 10/2003 | Jentzsch et al. |
| 2003/0207834 A1 | 11/2003 | Dale et al. |
| 2003/0212114 A1 | 11/2003 | Sato |
| 2003/0215406 A1 | 11/2003 | Schreiner et al. |
| 2003/0219472 A1 | 11/2003 | Pauletti et al. |
| 2004/0028614 A1 | 2/2004 | Corbella et al. |
| 2004/0034107 A1 | 2/2004 | Enzmann |
| 2004/0043045 A1 | 3/2004 | Seipel et al. |
| 2004/0047896 A1 | 3/2004 | Malnoe et al. |
| 2004/0049022 A1 | 3/2004 | Nyce et al. |
| 2004/0063648 A1 | 4/2004 | Pandol et al. |
| 2004/0063661 A1 | 4/2004 | Linnane |
| 2004/0067260 A1 | 4/2004 | Milley et al. |
| 2004/0082522 A1 | 4/2004 | Nyce |
| 2004/0086538 A1 | 5/2004 | Sauermann et al. |
| 2004/0109880 A1 | 6/2004 | Pauly et al. |
| 2004/0110848 A1 | 6/2004 | Peffley et al. |
| 2004/0115181 A1 | 6/2004 | Fujii et al. |

(56) References Cited

U.S. PATENT DOCUMENTS

| | | |
|---|---|---|
| 2004/0122109 A1 | 6/2004 | Fujii et al. |
| 2004/0126367 A1 | 7/2004 | Fujii et al. |
| 2004/0142006 A1 | 7/2004 | Bleckmann et al. |
| 2004/0142007 A1 | 7/2004 | Moussou et al. |
| 2004/0142009 A1 | 7/2004 | Ansmann et al. |
| 2004/0151710 A1 | 8/2004 | Bozzacco |
| 2004/0170581 A1 | 9/2004 | Henry et al. |
| 2004/0185071 A1 | 9/2004 | Hatazaki |
| 2004/0191190 A1 | 9/2004 | Pauly et al. |
| 2004/0191263 A1 | 9/2004 | Hageman et al. |
| 2004/0197279 A1 | 10/2004 | Bleckmann et al. |
| 2004/0197354 A1 | 10/2004 | Doring et al. |
| 2004/0202740 A1 | 10/2004 | Tan |
| 2004/0219114 A1 | 11/2004 | Andersson et al. |
| 2004/0228910 A1 | 11/2004 | Enzmann et al. |
| 2004/0234559 A1 | 11/2004 | Bleckmann et al. |
| 2004/0253323 A1 | 12/2004 | Giles |
| 2004/0258717 A1 | 12/2004 | Sauermann et al. |
| 2005/0000390 A1 | 1/2005 | Nieendick et al. |
| 2005/0008581 A1 | 1/2005 | Parkhideh |
| 2005/0019268 A1 | 1/2005 | Enzmann |
| 2005/0019278 A1 | 1/2005 | Berg-Schultz |
| 2005/0019353 A1 | 1/2005 | Prinz et al. |
| 2005/0025756 A1 | 2/2005 | Erwin |
| 2005/0026848 A1 | 2/2005 | Robinson et al. |
| 2005/0026850 A1 | 2/2005 | Robinson et al. |
| 2005/0036976 A1 | 2/2005 | Rubin et al. |
| 2005/0037036 A1 | 2/2005 | Nielsen et al. |
| 2005/0037102 A1 | 2/2005 | Tan et al. |
| 2005/0043336 A1 | 2/2005 | Hennequin et al. |
| 2005/0058610 A1 | 3/2005 | Baschong et al. |
| 2005/0069582 A1 | 3/2005 | Fantuzzi |
| 2005/0070610 A1 | 3/2005 | Fujii et al. |
| 2005/0070611 A1 | 3/2005 | Fantuzzi |
| 2005/0079164 A1 | 4/2005 | Fantuzzi et al. |
| 2005/0100537 A1 | 5/2005 | Evans et al. |
| 2005/0106190 A1 | 5/2005 | Kawa et al. |
| 2005/0106199 A1 | 5/2005 | Schreiber et al. |
| 2005/0112156 A1 | 5/2005 | Busch et al. |
| 2005/0118209 A1 | 6/2005 | Jentzsch et al. |
| 2005/0136081 A1 | 6/2005 | Kawa et al. |
| 2005/0142123 A1 | 6/2005 | Chen et al. |
| 2005/0142153 A1 | 6/2005 | Schreiber et al. |
| 2005/0147598 A1 | 7/2005 | Ueda et al. |
| 2005/0148603 A1 | 7/2005 | Jimenez et al. |
| 2005/0152856 A2 | 7/2005 | Andersson et al. |
| 2005/0184275 A1 | 8/2005 | Mora-Gutierrez et al. |
| 2005/0202521 A1 | 9/2005 | Crum |
| 2005/0214333 A1 | 9/2005 | Lanzendoerfer et al. |
| 2005/0220726 A1 | 10/2005 | Pauly et al. |
| 2005/0220826 A1 | 10/2005 | Kawa et al. |
| 2005/0226824 A1 | 10/2005 | Kawa et al. |
| 2005/0226858 A1 | 10/2005 | Kitamura et al. |
| 2005/0226947 A1 | 10/2005 | Kern |
| 2005/0238679 A1 | 10/2005 | Biergiesser et al. |
| 2005/0239721 A1 | 10/2005 | Rosenbloom |
| 2005/0255057 A1 | 11/2005 | Andre et al. |
| 2005/0276764 A1 | 12/2005 | Kolbe et al. |
| 2005/0281772 A1 | 12/2005 | Bromley et al. |
| 2005/0287206 A1 | 12/2005 | Fantuzzi et al. |
| 2005/0288333 A1 | 12/2005 | Kern |
| 2006/0002964 A9 | 1/2006 | Schreiber et al. |
| 2006/0008482 A1 | 1/2006 | Prinz et al. |
| 2006/0010519 A1 | 1/2006 | Kadowaki et al. |
| 2006/0013888 A1 | 1/2006 | Fantuzzi |
| 2006/0035981 A1 | 2/2006 | Mazzio et al. |
| 2006/0039956 A1 | 2/2006 | Hensen et al. |
| 2006/0041017 A1 | 2/2006 | Chopra |
| 2006/0051462 A1 | 3/2006 | Wang |
| 2006/0052438 A1 | 3/2006 | Ho et al. |
| 2006/0062755 A1 | 3/2006 | Woodward |
| 2006/0069068 A1 | 3/2006 | Kajander et al. |
| 2006/0073106 A1 | 4/2006 | Berg-Schultz et al. |
| 2006/0093633 A1 | 5/2006 | Stab et al. |
| 2006/0099158 A1 | 5/2006 | Zander et al. |
| 2006/0099244 A1 | 5/2006 | Guilford |
| 2006/0110415 A1 | 5/2006 | Gupta |
| 2006/0120997 A1 | 6/2006 | Lipton |
| 2006/0121016 A1 | 6/2006 | Lee |
| 2006/0127384 A1 | 6/2006 | Capaccioli et al. |
| 2006/0127928 A1* | 6/2006 | Bacus ............... C12Q 1/6886 435/6.14 |
| 2006/0128643 A1 | 6/2006 | Kaddurah-Daouk et al. |
| 2006/0153783 A1 | 7/2006 | Ehlis et al. |
| 2006/0188459 A1 | 8/2006 | Heinrichs et al. |
| 2006/0188492 A1 | 8/2006 | Richardson et al. |
| 2006/0193905 A1 | 8/2006 | Ehringer et al. |
| 2006/0205771 A1 | 9/2006 | Noble et al. |
| 2006/0251690 A1 | 11/2006 | Lipshutz et al. |
| 2006/0251708 A1 | 11/2006 | Chen et al. |
| 2006/0286046 A1 | 12/2006 | Haber |
| 2006/0292220 A1 | 12/2006 | Giordano et al. |
| 2007/0021360 A1 | 1/2007 | Nyce et al. |
| 2007/0026072 A1 | 2/2007 | Olsen et al. |
| 2007/0053985 A1 | 3/2007 | Ueda et al. |
| 2007/0071779 A1 | 3/2007 | McKie |
| 2007/0085059 A1 | 4/2007 | Mora-Gutierrez et al. |
| 2007/0092469 A1 | 4/2007 | Jacobs |
| 2007/0104701 A1 | 5/2007 | Ueda et al. |
| 2007/0104810 A1 | 5/2007 | Kern |
| 2007/0110731 A1 | 5/2007 | Riley |
| 2007/0129428 A1 | 6/2007 | Richelle et al. |
| 2007/0149618 A1 | 6/2007 | Cuevas Sanchez et al. |
| 2007/0172436 A1 | 7/2007 | Zhang |
| 2007/0184041 A1 | 8/2007 | Burja |
| 2007/0184076 A1 | 8/2007 | Unger et al. |
| 2007/0189994 A1 | 8/2007 | Berg et al. |
| 2007/0196349 A1 | 8/2007 | Kitamura et al. |
| 2007/0196914 A1 | 8/2007 | Murray et al. |
| 2007/0202090 A1 | 8/2007 | Prosek et al. |
| 2007/0218042 A1 | 9/2007 | Khaled |
| 2007/0225255 A1 | 9/2007 | Frohlich et al. |
| 2007/0243180 A1 | 10/2007 | Tanaka et al. |
| 2007/0248590 A1 | 10/2007 | Milne et al. |
| 2007/0248693 A1 | 10/2007 | Mazzio et al. |
| 2007/0253941 A1 | 11/2007 | Naidu et al. |
| 2007/0258966 A1 | 11/2007 | Ueda et al. |
| 2007/0258967 A1 | 11/2007 | Ueda et al. |
| 2007/0275021 A1 | 11/2007 | Lee et al. |
| 2008/0020018 A1 | 1/2008 | Moodley et al. |
| 2008/0020022 A1 | 1/2008 | Udell |
| 2008/0025929 A1 | 1/2008 | Burton et al. |
| 2008/0031862 A1 | 2/2008 | Ghosal |
| 2008/0057116 A1 | 3/2008 | Pleva |
| 2008/0063674 A1 | 3/2008 | Vollhardt et al. |
| 2008/0069779 A1 | 3/2008 | Tamarkin et al. |
| 2008/0069898 A1 | 3/2008 | Smith et al. |
| 2008/0075684 A1 | 3/2008 | Barg et al. |
| 2008/0081034 A1 | 4/2008 | Zimmerman et al. |
| 2008/0081082 A1 | 4/2008 | Zimmerman et al. |
| 2008/0089852 A1 | 4/2008 | Hotz et al. |
| 2008/0089913 A1 | 4/2008 | Kallmayer et al. |
| 2008/0095719 A1 | 4/2008 | Herrmann et al. |
| 2008/0102313 A1 | 5/2008 | Nilsen et al. |
| 2008/0260878 A1 | 10/2008 | Harano et al. |
| 2008/0287541 A1 | 11/2008 | Hoffman et al. |
| 2009/0010917 A1 | 1/2009 | Rosenblum et al. |
| 2009/0137556 A1 | 5/2009 | Bonnichsen |
| 2010/0209388 A1 | 8/2010 | Mazzio et al. |
| 2011/0136231 A1 | 6/2011 | Narain et al. |
| 2014/0255372 A1 | 9/2014 | Hsia et al. |

FOREIGN PATENT DOCUMENTS

| | | |
|---|---|---|
| JP | 2001514209 A | 9/2001 |
| WO | WO-1993016704 | 9/1993 |
| WO | WO-199505164 | 2/1995 |
| WO | WO-1996017626 | 6/1996 |
| WO | WO-1998035660 | 8/1998 |
| WO | WO-1999011242 | 3/1999 |
| WO | WO-2000007607 | 2/2000 |
| WO | WO-2002062329 | 8/2002 |
| WO | WO-2002078727 | 10/2002 |
| WO | WO-2002085297 | 10/2002 |

(56) References Cited

FOREIGN PATENT DOCUMENTS

| WO | WO-2003008405 | 1/2003 |
|---|---|---|
| WO | WO-2004003564 | 1/2004 |
| WO | WO-2005069916 | 8/2005 |
| WO | WO-2006017494 | 2/2006 |
| WO | WO-2006063402 | 6/2006 |
| WO | WO-2006108905 | 10/2006 |

OTHER PUBLICATIONS

Bliznakov, E., et al., "Coenzymes Q: Stimulants of the Phagocytic Activity in Rats and Immune Response in Mice", Experientia, 26(9): 953-954 (Sep. 1970).

Conklin KA (2004) Cancer Chemotherapy and Antioxidants, J.Nutr. 134:3201S-3204S.

Crane FL (2000) New Functions for Coenzyme Q10, Protoplasm, 213:127-133.

De Oliveria (1998) A Nutritious Cocktail for the Treatment of Melanoma: A Case Report, Journal of Orthomolecular Medicine, 13(3).

Folkers, K., et al., "Survival of Cancer Patients on Therapy with Coenzyme Q10", Biochemical and Biophysical Research Communication, vol. 192: 241-245 (1993).

Hodges, et al., "CoQ10: could it have a role in cancer management?", BioFactors, vol. 9, pp. 365-370 (1999).

Kawase I (1978) Enhancing Effect of Coenzyme Q10 on Immunorestoration with *Mycobacterium bovia* BCG in Tumor-Bearing Mice Gann, 69(4):493-497.

Kokawa, T., et al., "Coenzyme Q10 in cancer chemotherapy—experimental studies on augmentation of the effects of masked compounds, especially in the combined chemotherapy with immunopotentiators", XP002473825 Database accession No. NLM6881995(Abstract) (Mar. 1983).

Lamson et al. "Antioxidants in Cancer Therapy; Their Actions and Interactions With Oncologic Therapies" Alternative Medicine Review, vol. 4,No. 5, 1999, pp. 304-329.

Larsson O (1994) Effets of Isoprenoids on Growth of Normal Human Mammary Epithelial Cells and Breast Cancer Cells in vitro. Anticancer Research 14:123-128.

Li, GJ (1987) Protective Effect of Coenzyme Q10 against the Adverse Reaction of Mytomycin G in Mouse Liver Acta Histochemica et Cytochemica 1087, 20(4):455-467.

Lockwood, et al., "Apparent partial remission of breast cancer in 'high risk' patients supplemented with nutritional antioxidants, essential fatty acids and coenzyme Q10", Mol-Aspects-Med., vol. 15 Suppl. pp. 231-240 (1994) (Abstract Only).

Lockwood, et al., "Partial and complete regression of breast cancer in patients in relation to dosage of coenzyme Q10", Biochem-Biophys-Res-Commun., 199(3), pp. 1504-1508 (1994) (Abstract Only).

Lockwood, et al., "Progress on Therapy of Breast Cancer with Vitamin Q10 and the Regression of Metastases", Biochem-Biophys-Res-Commun 212(1) pp. 172-177 (1995).

Palan PR et al (2003) Plasma Concentrations of Coenzyme Q10 and Tocopherols in Cervical Intraepithelial Neoplasia and Cervical Cancer. Eur. J. Cancer Prev. 12:321-326.

Roffe et al (2004) Efficacy of Coenzyme Q10 for Improved Tolerability of Cancer Treatments: A Systematic Review. J. Clin. Oncol. 22:4418-24.

Seifried, et al., the antioxidant conundrum in cancer. Cancer Res. 2003, 63(15):4295-8.

Shekelle P, et al. (2003) Effect of the Supplemental Use of Antioxidants Vitamin C, Vitamin E, and Coenzyme Q10 for the Prevention and Treatment of Cancer. Evid. Rep. Technol. Assess. 75:1-3.

Shimizu T (2003) Paclitaxel Pirarubicin Weekly. Japan J. Cancer and Chemotherapy 30:105-109.

The National Cancer Institute, "Coenzyme Q10 (PDQ.RTM.) Patient Version", http://www.cancer.gov/cancertopics/pdq/cam/coenzymeQ10/patient/allpages; Jul. 10, 2009.

Women's Health Update: Coenzyme Q10 and Breast Cancer, http://www.encognitive.com/node/13574, downloaded Dec. 26, 2012.

Ansell, et al., "Brain Tumor Signs and Symptoms: Analysis of Primary Health Care Records from the UKCCS", Pediatrics 125(1): pp. 112-119 (2009).

Persaud et al., "Attenuation of tumor angiogenesis in murine melanoma model using liposomal formulation of Coenzyme Q10", Proc. Amer. Assoc. Cancer Res. 47: Abst. No. 997, 2006.

Tucker et al., "Group IVC cytosolic phospholipase A2 is farnesylated and palmitoylated in 2,11,16 mammalian cells", J. Lipid Res. 46:2122-33, 2006.

Haupt et al., "Apoptosis—the p53 network", J. Cell Sci. 116: 4077-85, 2003.

Graos et al., "Growth-factor-dependent phosphorylation of Bim in mitosis", Biochem J.388:185-194, 2005.

Narain, et al., "Topical formulation of Coenzyme Q10 inhibits growth of melanoma tumors", J. Invest. Derm. 122:A160, 2004.

Narain et al., "Coenzyme Q10 attenuates angiogenesis in melanoma", J. Invest. Derm. 124:A24, 2005.

Narain, et al., "Coenzyme Q10: A novel Bcl-2 drug target for the treatment of melanoma", Proceedings of the American Associate for Cancer Research, (2006); 47:A791, 2006.

Narain, et al., "Coenzyme Q10 induces apoptosis in human melanoma cells", J. Invest. Derm. 122(3): A160, 2004.

Sorenson et al., "Bcl-2 family members and disease", Biochem. Biophys. Acta., 1644(2-3), 169-177, 2004.

Basu et al., "The relationship between Bcl2, Bax and p53: consequences for cell cycle progression and cell death", Molecular Human Reproduction 3: 1099-1109, 1998.

Appel et al., 2000, "Differential Regulation of Bcl-2 and Bax Expression in Cells Infected with Virulent and Nonvirulent Strains of Sindbis Virus", Virology 276: 238-242.

Kirkin et al., 2004, "The Role of Bcl-2 Family Members in Tumorigenesis", Biochimica et Biophysica Acta 1644: 229-249.

Gross et al., 1999, "BCL-2 Family Members and the Mitochondria in Apoptosis", Genes & Development 13: 1899-1911.

U.S. Pat. No. 8,147,825, Apr. 3, 2012, Granted.
U.S. Pat. No. 8,293,227, Oct. 23, 2012, Granted.
U.S. Pat. No. 8,586,030, Nov. 19, 2013, Granted.
U.S. Pat. No. 8,562,976, Oct. 22, 2013, Granted.
U.S. Pat. No. 8,771,680, Jul. 8, 2014, Granted.
U.S. Appl. No. 14/282,336, filed May 20, 2014, US 2014/0255372, Pending.
U.S. Pat. No. 9,205,064, Dec. 8, 2015, Granted.
U.S. Appl. No. 14/940,614, filed Nov. 13, 2015, US 2016/0145693, Pending.
U.S. Appl. No. 12/778,010, filed May 11, 2010, US 2011/0123986, Abandoned.
U.S. Appl. No. 15/011,196, filed Jan. 29, 2016, Pending.

\* cited by examiner

Skmel-28 cells were incubated with Q10 for 24 hrs. Cells were harvested and quantified for Bcl-2 expression.

Reduction in Angiogenesis in Melanoma tumors treated with

Ctrl

Treatment

Bcl-2 expression in SkBr3 after 4 hrs Rx

METHODS AND USE OF INDUCING APOPTOSIS IN CANCER CELLS

CROSS-REFERENCE TO RELATED APPLICATIONS

This application is a continuation of U.S. application Ser. No. 14/177,171, filed Feb. 10, 2014, which is a continuation of U.S. application Ser. No. 13/345,570, filed Jan. 6, 2012, which is a continuation of U.S. application Ser. No. 12/936,852, filed on Jan. 27, 2011, which is a 371 application of International Application No. PCT/US2009/039992, filed Apr. 9, 2009, which claims the benefit of priority to U.S. Provisional Patent Application No. 61/044,085, filed on Apr. 11, 2008. The entire contents of each of the above-mentioned priority applications are hereby incorporated by reference in their entirety.

BACKGROUND

Programmed cell death (apoptosis) is integral to the sustenance of life as the constant renewal of tissue provides the physiologic scaffold for regenerative metabolism. Apoptosis facilitates the homeostatic balance of cellular renewal allowing for overall tissue health, so that the integrity of proliferative, immunomodulatory, and angiogenic components of tissue metabolism are maintained. A dysregulation in any one of, or a combination of, the aforementioned processes may result in a lack of apoptotic control. Such lack of apoptotic control, optionally in combination with genetic mutations, may result in a favorable oncogenic environment.

Under healthy conditions, the genome's "watchman," p53, recognizes when a cell's integrity is compromised and commits it to apoptosis via employment of the Bcl-2 protein family in the mitochondria leading to nuclear fragmentation. See, e.g., Selivanova, at al., "Reactivation of mutant p53: molecular mechanisms and therapeutic potential," Oncogene (2007) 26, 2243-2254.

Moreover, the balance of the "pro" and "anti" apoptotic members of the Bcl-2 protein family may determine the overall apoptotic potential for a cell. In over 60% of all cancers, p53 is mutated or inactivated and the Bcl-2 protein is overexpressed, leading to a resistance to cell death and chemotherapeutic approaches.

It has been shown that cancer patients have an overall decreased serum level of CoQ10 which may lead to sign and symptoms of malaise, weakness, and lethargy, especially when using chemotherapeutic modalities. See, e.g., Okamoto, et al. "Serum levels of coenzyme Q10 and lipids in patients during total parenteral nutrition," J Nutr Sci Vitaminol (Tokyo), (1986) February; 32(1):1-12. Studies from the University of Miami using an athymic mouse model have demonstrated that a liposomal formulation of CoQ10 reduced human melanoma tumors by 53.2% in 30 days while an overall attenuation of tumor angiogenesis was observed. See, e.g., Persaud, et al., "Attenuation of tumor angiogenesis in murine melanoma model using liposomal formulation of Coenzyme Q10," Proceedings of the American Association for Cancer Research, (2006); 47:A977. In addition, it was subsequently shown that the effect of CoQ10 was mediated by a downregulation of the Bcl-2 protein. See, e.g., Narain, et al., "Coenzyme Q10: A novel Bcl-2 drug target for the treatment of melanoma," Proceedings of the American Association for Cancer Research, (2006); 47:A791.

Drugs have been developed to target the Bcl2 protein family either by direct antibody inhibition or by the use of specific constructs that interfere with binding, which may lead to dimerization or oligomerization, in an effort to restore the balance of the pro- and anti-apoptotic proteins. See, e.g., U.S. Pat. Nos. 6,514,761 and 6,040,181. However, this does not fundamentally alter the upstream levels of the major apoptotic members of the Bcl-2 protein family, such as Bcl-2, Bax, and Bid, following a re-activation of p53 which enables the given cell to undergo apoptosis.

SUMMARY

The present disclosure describes a method of delivering CoQ10 or its metabolites into a cell and forming a complex with endogenous CoQ10 and membrane lipids that induces the activation of p53 and initiation of Bcl-2 mediated apoptosis in a cancer cell by modulation of the Bcl-2 subfamily members.

In embodiments, the present disclosure provides a composition including CoQ10 and phospholipid liposomes that binds to endogenous lipids that maintain membrane integrity such as oleic acid in addition to mevalonic acid and quinones. The present disclosure is also directed to methods of activating p53 and modulating the expression of the Bcl-2 protein family in a manner that commits a given cell to undergo apoptosis where that cell is an oncogenic cell.

In embodiments, the present disclosure provides a composition for the treatment of cancer including CoQ10, liposomes, and a pharmaceutically acceptable carrier. In some embodiments, the composition includes between about 0.001% to about 60% (w/w) of Coenzyme Q10.

In other embodiments, the composition may be in the form of a gel, ointment, cream, salve, lotion, mousse, foam, spray and/or aerosol, liquid (intravenous), nebulized powder, suppository, or any other commercially feasible parenteral route.

In other embodiments, the present disclosure provides a method of treating cancer which includes administering to a patient in need thereof, a composition including a therapeutically effective amount of CoQ10, liposomes, and a pharmaceutically acceptable carrier to the area of oncogenesis. In embodiments, the composition includes between about 0.001% to about 60% (w/w) of Coenzyme Q10.

In other embodiments, the present disclosure provides a method of contacting endogenous CoQ10 by administering to a patient in need thereof, a composition including a therapeutically effective amount of CoQ10, liposomes and a pharmaceutically acceptable carrier to the area of oncogenesis. The composition may include between about 0.001% to about 60% (w/w) of Coenzyme Q10.

The present disclosure also provides a method of targeting the Bcl-2 family of proteins which includes administering to a patient in need thereof a composition including a therapeutically effective amount of CoQ10, liposomes, and a pharmaceutically acceptable carrier to the area of oncogenesis. In embodiments, the composition includes between about 0.001% to about 60% (w/w) of Coenzyme Q10.

The present disclosure also provides a method of re-activating the p53 protein which includes administering to a patient in need thereof a composition including a therapeutically effective amount of CoQ10, liposomes, and a pharmaceutically acceptable carrier to the area of oncogenesis. In embodiments, the composition includes between about 0.001% to about 60% (w/w) of Coenzyme Q10.

The present disclosure also provides a method of modulating the BH3 binding domains of the Bcl-2 family (e.g. Bid, Bim, Bik) administering to a patient in need thereof, a composition including a therapeutically effective amount of CoQ10, liposomes and a pharmaceutically acceptable carrier to the area of oncogenesis. In embodiments, the composition includes between about 0.001% to about 60% (w/w) of Coenzyme Q10.

Methods of modulating the Bax protein are also provided which include, in embodiments, administering to a patient in need thereof a composition including a therapeutically effective amount of CoQ10, liposomes and a pharmaceutically acceptable carrier to the area of oncogenesis. In embodiments, the composition includes between about 0.001% to about 60% (w/w) of Coenzyme Q10.

The present disclosure also provides a method of modulating angiogenic factors such as VEGF, FGF, Hif-1α, and angiostatin by administering to a patient in need thereof a composition including a therapeutically effective amount of CoQ10, liposomes and a pharmaceutically acceptable carrier to the area of oncogenesis. In embodiments, the composition includes between about 0.001% to about 60% (w/w) of Coenzyme Q10.

In another embodiment, a method of modulating cell-cycle factors such as smad proteins, TGF-β, cdk's (cyclin-dependent kinases), and PI3K/akt administering to a patient in need thereof, a composition including a therapeutically effective amount CoQ10, liposomes and a pharmaceutically acceptable carrier to the area of oncogenesis. In embodiments, the composition includes between about 0.001% to about 60% (w/w) of Coenzyme Q10.

BRIEF DESCRIPTION OF THE DRAWINGS

The above and farther advantages of this disclosure may be better understood by referring to the following description taken in conjunction with the accompanying drawings, in which.

DETAILED DESCRIPTION

Figure 1:
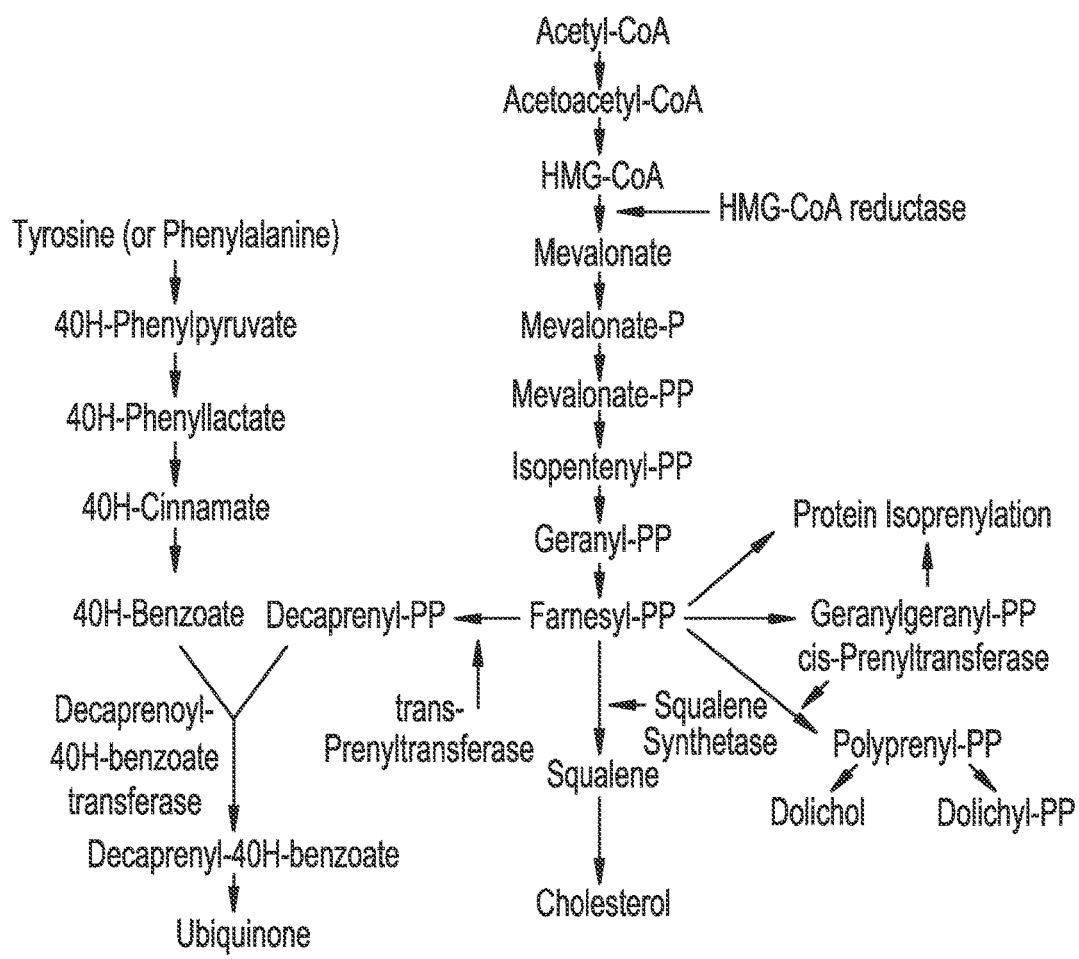
FIG. 1 is a depiction of the metabolic synthesis of CoQ10.

The present disclosure provides pharmaceutical compositions including Coenzyme Q10 (CoQ10) and methods of linking to endogenous lipid molecules to modulate molecular machinery that relates to an oncogenic state. The scope of the present disclosure relates to the fields of molecular medicine and oncology specific to gene modulation of the p53 pathway and Bcl-2 gene family.

Definitions

In accordance with the present disclosure and as used herein, the following terms are defined with the following meanings, unless explicitly stated otherwise.

As used herein, "a", "an," and "the" include plural references unless the context clearly dictates otherwise.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and therapeutic effective amount" refers to the quantity of a component which is sufficient to yield a desired therapeutic response without undue adverse side effects (such as toxicity, irritation, or allergic response) commensurate with a reasonable benefit/risk ratio when used in the manner of this disclosure. By "therapeutically effective amount" is meant an amount of a compound of the present disclosure effective to yield the desired therapeutic response. For example, accelerate wound healing, relief of pain and fatigue. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, a "pharmaceutical salt" include, but are not limited to, mineral or organic acid salts of basic residues such as amines; alkali or organic salts of acidic residues such as carboxylic acids. Suitable salts may be made using an organic or inorganic acid. Such salts include chlorides, bromides, sulfates, nitrates, phosphates, suffocates, formates, tartrates, maleates, malates, citrates, benzoates, salicylates, ascorbates, and the like. In embodiments, hydrochloride salt may be utilized.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "patient" or "individual" are used interchangeably herein, and refers to a mammalian subject to be treated, with human patients being suitable in some embodiments. In some cases, the methods of the present disclosure find use in experimental animals, in veterinary application, and in the development of animal models for disease, including, but not limited to, rodents including mice, rats, and hamsters; and primates.

"Sample" is used herein in its broadest sense. A sample including polynucleotides, polypeptides, peptides, antibodies and the like may include a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. As used herein, "ameliorated" or "treatment" refers to a symptom which is approaches a normalized value (for example a value obtained in a healthy patient or individual), e.g., is less than 50% different from a normalized value, in embodiments less than about 25% different from a normalized value, in other embodiments is less than 10% different from as normalized value, and in yet other embodiments the presence of a symptom is not significantly different from a normalized value as determined using routine statistical tests.

As used herein, "an ameliorated symptom" or "treated symptom" refers to a symptom which is approaches a normalized value, e.g., is less than 50% different from a normalized value, in embodiments less than about 25% different from a normalized value, in other embodiments less than about 10% different from a normalized value, and yet other embodiments the presence of a symptom is not significantly different from a normalized value as determined using routine statistical tests.

Subjects

Subjects from many different species can be treated with the compositions of the present disclosure. A non-exhaustive exemplary list of such animals includes mammals such as mice, rats, rabbits, goats, sheep, pigs, horses, cattle, dogs, cats, and primates such as monkeys, apes, and human beings. Those animal subjects known to suffer muscle fatigue, pain, wounds, and the like may be suitable for use in the present disclosure, in particular, human patients suffering from injuries, surgery, arthritis, muscle fatigue and the like are suitable animal subjects for use in the present disclosure. By adapting the methods taught herein to other methods known in medicine or veterinary science (e.g., adjusting doses of administered substances according to the weight of the subject animal), the compositions utilized in the present disclosure can be readily optimized for use in other animals.

Pharmaceutical Compositions and Administration to a Subject

In embodiments, the present disclosure provides CoQ10 compositions for the treatment and prevention of cancer. Transdermal, oral intravenous, and other parenteral preparations of 2, 3-dimethoxy-5-methyl-6-decaprenyl-1,4-benzoquinone (coenzyme Q-10) may include, inter alia, auxiliary agents, an effective amount of pulmonary surfactant, end/or in combination with liposomes.

In embodiments, the compositions including CoQ10 may be administered topically. It may be desirable to present the active ingredient, e.g. CoQ10, as a pharmaceutical formulation, Exemplary compositions are described in detail in the examples which follow. The active ingredient may include, for topical administration, from 0.001% to about 60% w/w, by weight of the formulation in the final product, although it may include as much as 80% w/w, in embodiments from about 0.001% to about 60% w/w of the formulation. The topical formulations of the present disclosure, include an active ingredient together with one or more acceptable carrier(s) thereof and optionally any other therapeutic ingredients(s). The carrier(s) must be "acceptable" in the sense of being compatible with the other ingredients of the formulation and not deleterious to the recipient thereof.

In some embodiments, the CoQ10 may be included in a composition such as the composition disclosed in U.S. patent application Ser. No. 12/052,825, the entire disclosure of which is incorporated by reference herein.

The composition of the present disclosure can be administered to a patient either by themselves, or in pharmaceutical compositions where it is mixed with suitable carriers or excipient(s). In treating a patient exhibiting a disorder of interest, a therapeutically effective amount of an agent or agents such as these is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices may be desirable. The data obtained from these cell culture assays and animal studies can be used in formulating a range of dosage for use in human. The dosage of such compounds may be within a range of circulating concentrations that include the ED with little or no toxicity. The dosage may vary within this range depending upon the dosage form employed and the route of administration utilized.

For any compound used in the method of the present disclosure, the therapeutically effective dose can be estimated initially from cell culture assays. For example, a dose can be formulated in animal models to achieve a circulating plasma concentration range that includes the $IC_{50}$ as determined in cell culture. Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above for humans may be used in veterinary medicine.

The compositions of the present disclosure can be applied to a patient by treatment modalities that are tailored to the patient, such as the type of injury, severity of the injury, location of the injury. For example, the percentage of the active composition can be modulated during the course of treatment again depending on severity, type of injury etc. CoQ10 the active ingredient, may include, from 0.001% to about 60% w/w, by weight of the formulation in the final product, although it may include as much as 80% w/w, in embodiments from about 0.001% to about 60% w/w of the formulation.

The compositions can be applied to a patient at least once a day. In other embodiments the pharmaceutical compositions can be applied, twice a day, three times a day or more. The times and compositions containing the active ingredients can easily be determined by a clinician.

Depending on the specific conditions being treated, such agents may be formulated and administered systemically or locally. Techniques for formulation and administration may be found in Remington's Pharmaceutical Sciences, 18$^{th}$ ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

The compositions described above may be administered to a subject in any suitable formulation. In addition to treatment of cancer with topical formulations of CoQ10, in other aspects of the present disclosure CoQ10 might be delivered by other methods. For example, CoQ10 might be formulated for parenteral delivery, e.g., for subcutaneous, intravenous, intramuscular, or intratumoral injection. Other methods of delivery, for example, liposomal delivery or diffusion from a device impregnated with the composition might be used. The compositions may be administered in a single bolus, multiple injections, or by continuous infusion (for example, intravenously or by peritoneal dialysis). For parenteral administration, the compositions may be formulated in a sterilized pyrogen-free form. Compositions of the present disclosure can also be administered in vitro to a cell (for example, to Bcl-2 production in a cell or in an in vitro culture) by simply adding the composition to the fluid in which the cell is contained.

Depending on the specific conditions being treated, such agents may be formulated and administered systemically or locally. Techniques for formulation and administration may be found in Remington's Pharmaceutical Sciences, 18$^{th}$ ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the present disclosure may be formulated in aqueous solutions, for example, in physiologically compatible buffers such as Hanks' solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the present disclosure into dosages suitable for systemic administration is within the scope of the present disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the present disclosure to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers including excipients and auxiliaries which facilitate processing of the active compounds into preparations which can be used pharmaceutically. The preparations formulated for oral administration may be in the form of tablets, dragees, capsules, or solutions. The pharmaceutical compositions of the present disclosure may be manufactured in a manner that is itself known, e.g., by means of conventional mixing, dissolving, granulating, dragee-making, levitating, emulsifying, encapsulating, entrapping or lyophilizing processes.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose. Drops according to the present disclosure may include sterile aqueous or oily solutions or suspensions and may be prepared by dissolving the active ingredient in a suitable aqueous solution of a bactericidal and/or fungicidal agent and/or any other suitable preservative, and in some embodiments including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present disclosure include those suitable for application to the skin or eye. An eye lotion may include a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present disclosure are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may include hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol cellulose preparations such as, for example, maize starch, wheat starch, rice starch, potato starch, gelatin, gum tragacanth, methyl cellulose, hydroxypropylmethyl-cellulose, sodium carboxy-methylcellulose, and/or polyvinyl pyrrolidone (PVP). If desired, disintegrating agents may be added, such as the cross-linked polyvinyl pyrrolidone, agar, or alginic acid or a salt thereof such as sodium alginate.

Dragee cores are provided with suitable coating. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The composition can include a buffer system, if desired. Buffer systems are chosen to maintain or buffer the pH of compositions within a desired range. The term "buffer system" or "buffer" as used herein refers to a solute agent or agents which, when in a water solution, stabilize such solution against a major change in pH (or hydrogen ion concentration or activity) when acids or bases are added thereto. Solute agent or agents which are thus responsible for a resistance or change in pH from a starting buffered value in the range indicated above are well known. While there are countless suitable buffers, potassium phosphate monohydrate may be a suitable buffer.

The final pH value of the pharmaceutical composition may vary within the physiological compatible range. The final pH value should not be irritating to human skin and may also be selected so that transdermal transport of the active compound, e.g. CoQ10, may be facilitated. Without violating this constraint, the pH may be selected to improve CoQ10 compound stability and to adjust consistency when required. In one embodiment, the pH value may be from about 3 to about 7.4, in embodiments from about 3.2 to about 6.5, in other embodiments from about 3.5 to about 6.

In some embodiments, the remaining component of a topical delivery vehicle may be water, in embodiments purified, e.g. deionized, water. Such delivery vehicle compositions may contain water in an amount of from about 50 to about 95 percent, based on the total weight of the composition. The specific amount of water present is not critical, however, being adjustable to obtain the desired viscosity (usually about 50 cps to about 10,000 cps) and/or concentration of the other components. The topical delivery vehicle may have a viscosity of at least about 30 centipoises.

Other known transdermal skin penetration enhancers can also be used to facilitate delivery of CoQ10. Illustrative are sulfoxides such as dimethylsulfoxide (DMSO) and the like; cyclic amides such as 1-dodecylazacycloheptane-2-one (AZONE®, a registered trademark of Nelson Research, Inc.) and the like; amides such as N,N-dimethyl acetamide (DMA) N,N-diethyl toluamide, N,N-dimethyl formamide, N,N-dimethyl octamide, N,N-dimethyl decamide, and the like; pyrrolidone derivatives such as N-methyl-2-pyrrolidone, 2-pyrrolidone, 2-pyrrolidone-5-carboxylic acid, N-(2-hydroxyethyl)-2-pyrrolidone or fatty acid esters thereof, 1-lauryl-4-methoxycarbonyl-2-pyrrolidone, N-tallow alkylpyrrolidones, and the like; polyols such as propylene glycol, ethylene glycol, polyethylene glycol, dipropylene glycol, glycerol, hexanetriol, and the like; linear and branched fatty acids such as oleic, linoleic, lauric, valeric, heptancic, caproic, myristic, isovaleric, neopentanoic, trimethyl hexanoic, isostearic, and the like; alcohols such as ethanol, propanol, butanol, octanol, oleyl, stearyl, linoleyl, and the like; anionic surfactants such as sodium laurate, sodium leuryl sulfate, and the like; cationic surfactants such as benzalkonium chloride, dodecyltrimethylammonium chloride, cetyltrimethylammnonium bromide, and the like; non-ionic surfactants such as the propoxylated polyoxyethylene ethers, e.g., Poloxamer 231, Poloxamer 182, Poloxamer 184, and the like, the ethoxylated fatty acids, e.g., Tween 20, Myrj 45, and the like, the sorbitan derivatives, e.g., Tween 40, Tween 60, Tween 80, Span 60, and the like, the ethoxylated alcohols, e.g., polyoxyethylene (4) lauryl ether (Brij 30), polyoxyethylene (2) oleyl ether (Brij 93), and the like, lecithin and lecithin derivatives, and the like; the terpenes such as D-limonene, α-pinene, β-carene, α-terpineol, carvol, carvone, menthone, limonene oxide, α-pinene oxide, eucalyptus oil, and the like.

Also suitable as skin penetration enhancers are organic acids and esters such as salicylic acid, methyl salicylate, citric acid, succinic acid, and the like.

Effective Amounts

The compositions described above may be administered to a subject in an effective amount. An effective amount is an amount which is capable of producing a desirable result in a treated animal or cell. As is well known in the medical and veterinary arts, dosage for any one animal depends on many factors, including the particular animal's size, body surface area, age, the particular composition to be administered, time and route of administration, general health, and other drugs being administered concurrently. It is expected that an appropriate dosage for topical administration of the compositions of the present disclosure would be from about 0.1 to about 2.5 mg CoQ10/kg of body weight (e.g., from about 10 to about 500 mg for subjects ranging from about 110 to about 300 lbs. An effective amount for use with a cell in culture will also vary, but can be readily determined empirically (for example, by adding varying concentrations to the cell and selecting the concentration that best produces the desired result). It is expected that an appropriate concentration would be from about 1 to about 250 μM.

EXAMPLES

Materials utilized for the experiments to generate the data accompanying the present disclosure included the following: Skmel-28 (HTB-72), PC-3 (CRL-1435), and SkBr3 (HBT-30) were purchased from ATCC. The cell lines were grown in DMEM/F12 medium (Dulbecco's Modified Eagle Medium:Nutrient Mixture F-12, commercially available from Invitrogen Corporation) and supplemented with 5% bovine calf serum. The Bcl-2 (Cat #:2872), Bax (Cat #:2774), Bid (Cat #:2002), p53 (Cat #:9282), Bcl-xl (Cat #:2762), Caspase-3 (Cat #:9662), Mcl-1 (Cat #:4572), Bax (Cat #:2772), Anti-rabbit IgG1 (Cat #:7074), and Anti-Mouse IgG (Cat #:7076) antibodies were purchased from Cell Signaling Technology (Boston, Mass.). Reagents and chemicals were purchased from Sigma Aldrich (St Louis, Mo.). Western blot gels and buffers were purchased from Bio-Rad (Hercules, Calif.).

Example 1

Protein Expression Protocol.
(Generated the data found in FIGS. 3, 4, 5, 6, 7, 10a-10d, 13, 14, 16, 18, 19a, and 25.)

Skmel-28, PC-3, and SkBr3 cells were grown to 80% confluency and subcultured in petri dishes. After 24 hours, the cells adhered to the plates and the medium was extracted. Treatment medium was added to each plate. Following the intended incubation time, the medium was removed and the cells were washed with cold phosphate buffered saline (PBS). The cells were scraped in cold PBS and collected in centrifuge tubes. Cells were then pelleted and washed with cold PBS (3 times). The PBS was removed, after which a lysis buffer was added and sonicated to disperse the protein structures. A sample buffer was added to each tube and the solutions were boiled for 5 minutes. Using a BCA (bicinchoninic acid) protein analysis kit, the concentration of protein was quantified for each sample. These values determined the loading volumes for each samples.

The samples were loaded in a 4% stacking and 12% running Tris-Hcl gel western blot gels. After separation, the bands of protein were transferred to nitrocellulose paper using electrophoresis. The nitrocellulose paper was blocked overnight with 5% milk solutions. The respective antibodies were added to each nitrocellulose paper containing the protein samples. After 24 hours the primary antibody was removed and the extraction paper was washed to remove any unbounded primary antibodies. Depending on the type of the primary antibody, an anti-mouse or anti-rabbit secondary antibody was added to the protein extracts. After incubation, the antibodies were removed and the nitrocellulose papers were washed. A Pico Chemo-luminescent was added and the nitrocellulose paper was exposed to X-Ray development film under dark room conditions. The film was developed to record the protein expression.

Graphical Analysis for the Western Blot Analysis
(Generated the data found in FIGS. 12, 15, 17, 19a, 20, 21, 22, 23, 24, 26.)

The procedure for protein expression was used to obtain a photographic image of the protein expression. These imaged were scanned into image files for computer analysis. Using ImageJ software developed by the U.S. National Institutes of Health (NIH), the levels of protein expression were quantified. The expression was then calculated based on the level of expression of the actin, which was the loading control for the samples. The numerical values were statistically analyzed for statistical significance.

Histological Samples

Skmel-28 cells were grown in 5% serum supplemented DMEM/F12 medium to 80% confluency. The cells were trypsinized and pelleted using a centrifuge. The pellets were then resuspended in cold PBS. The subjects for this study were nude athymia mice. Each subject received two injections of the cell suspension on the dorsal region of the mouse. After a visual assessment of the establishment of a tumor, treatment with a topical application would commence. After 30 days of treatment, the tumors were excised from the mice and placed in formalin. Each tumor sample was embedded in paraffin and sliced using a microtome. The slides underwent an H & E or S-100 stain. These samples were than analyzed by a pathologist to assess the vascular integrity of the tumor.

Figure 2:
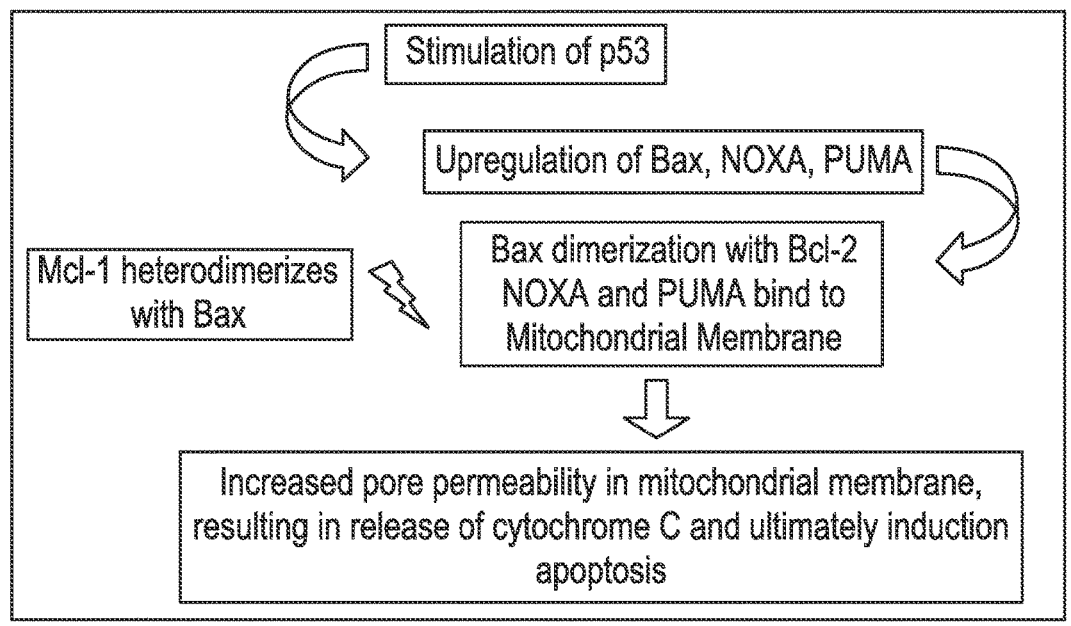
FIG. 2 is a summary of the interactions of Bax, P53, and Bcl-2 in the induction of apoptosis.
Figure 3:
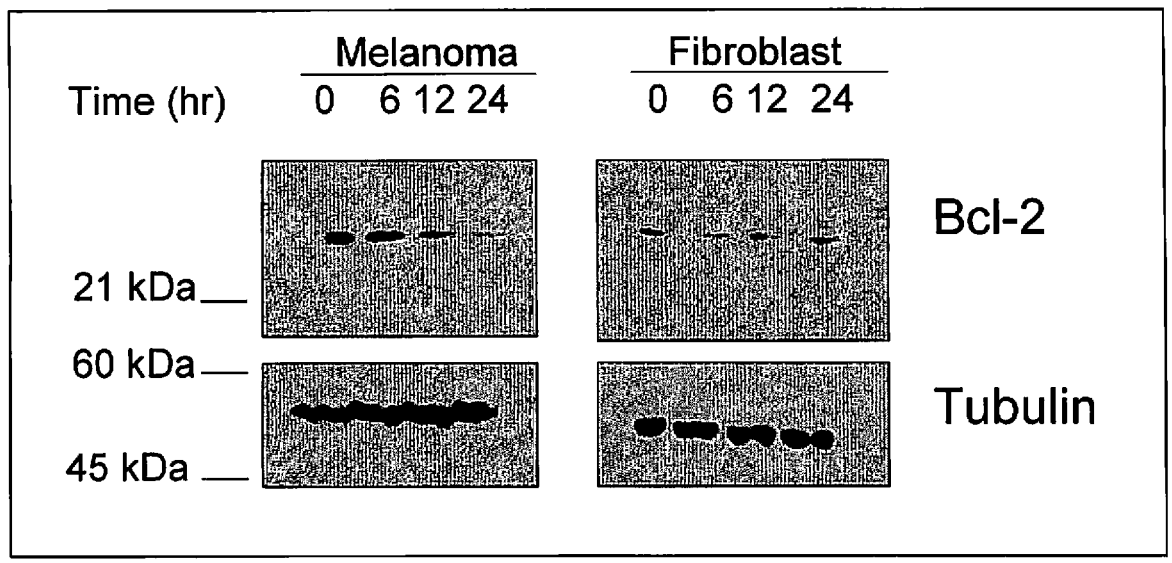
FIG. 3 shows Bcl-2 expression in melanoma cells and neonatal fibroblasts after treatment with 50 µM CoQ10.
Figure 4:
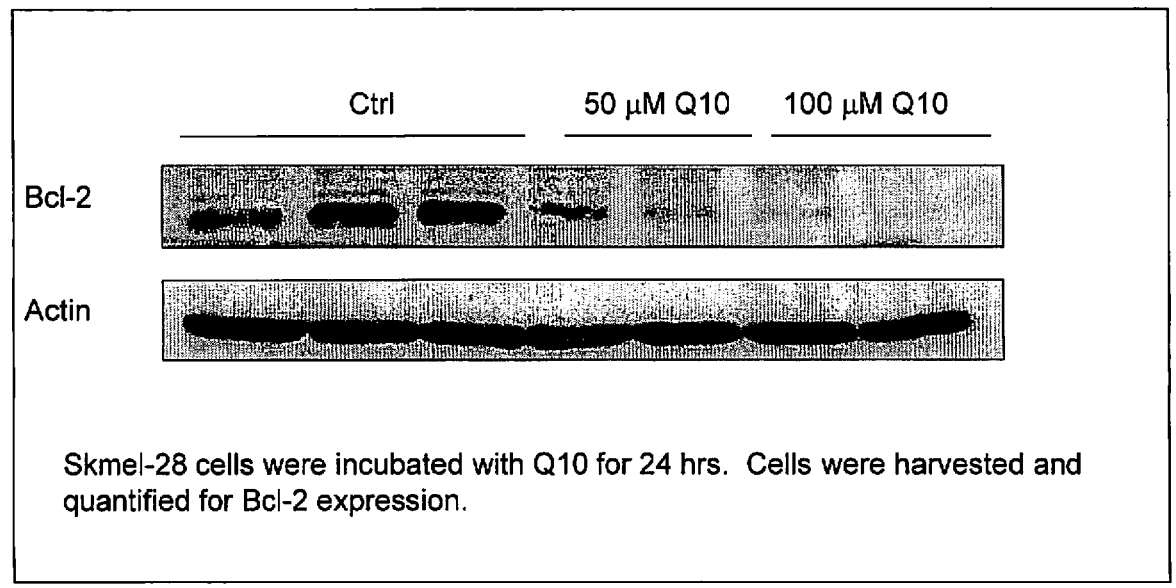
FIG. 4 shows Bcl-2 expression in melanoma cells incubated with 50 µM and 100 µM CoQ10 for 24 hours.
Figure 5:
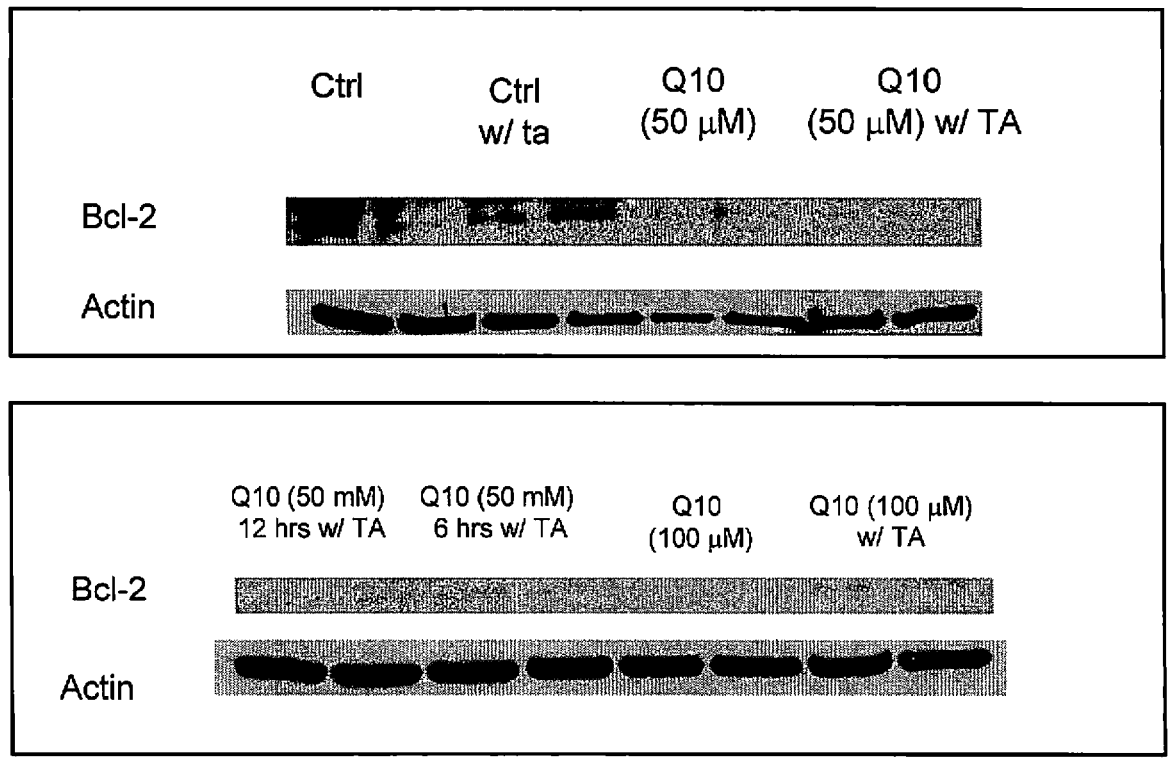
FIG. 5 shows Bcl-2 expression in melanoma cells treated in the presence and absence of CoQ10 using 24 hr Take Away (TA) method. In TA experiments melanoma cells were treated with CoQ10 for 6, 12, and 24 hours. After incubation the medium was replaced with normal culture medium for 24 hours. Bcl-2 expression was measured to assess the commitment to apoptosis.
Figure 6:
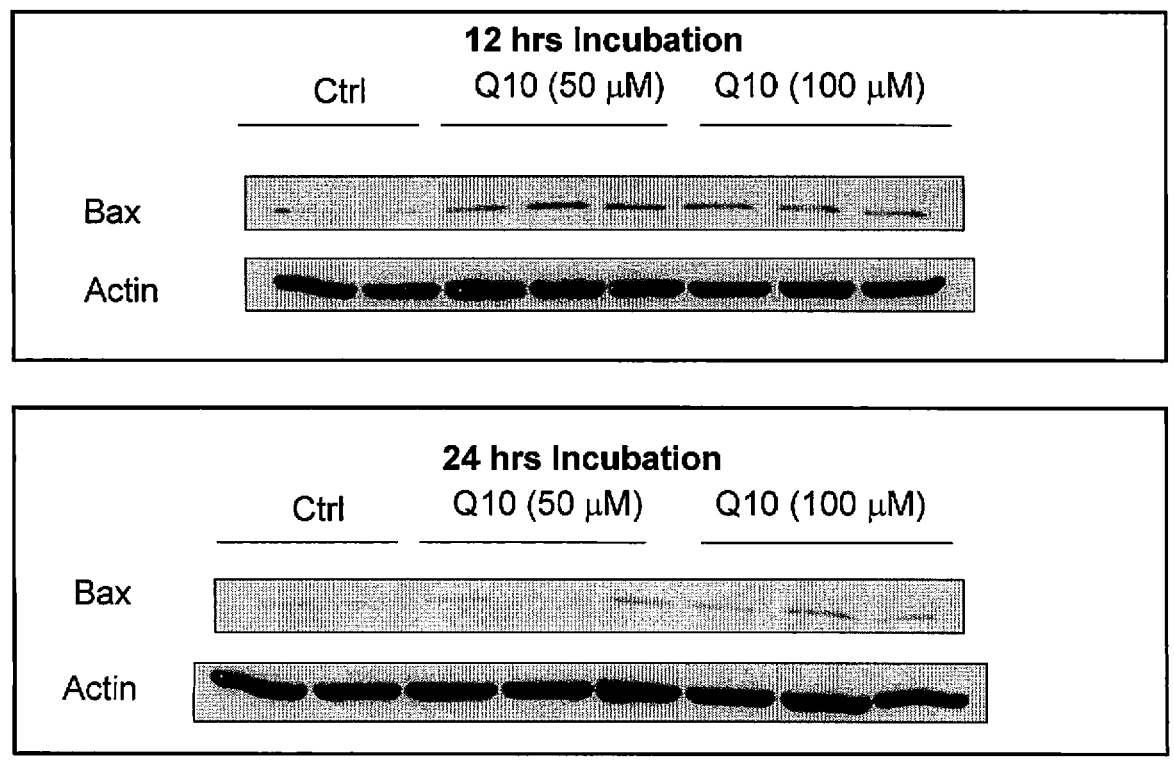
FIG. 6 shows Bax expression in melanoma cells after 12 and 24 hours incubation with CoQ10 (50 µM and 100 µM)
Figure 7:
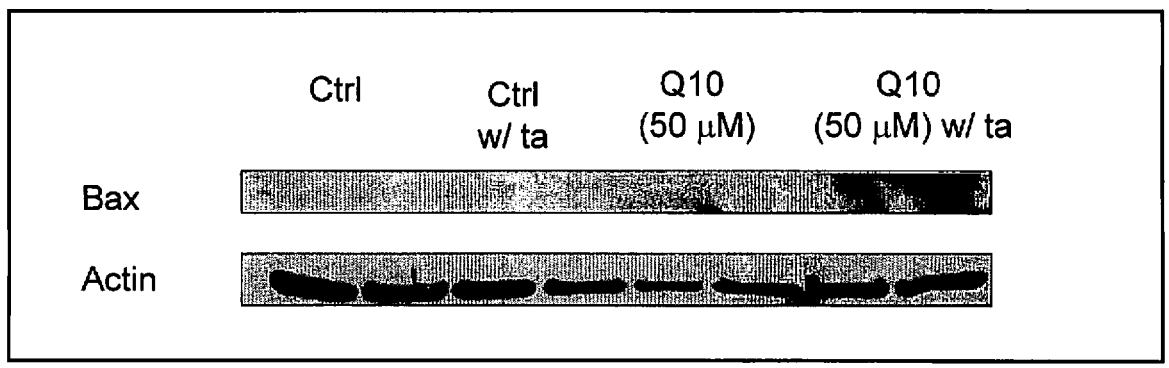
FIG. 7 shows Bax expression in melanoma cells treated in the presence and absence of CoQ10 using 24 hr Take Away (TA) method. In TA experiments melanoma cells were treated with CoQ10 for 6, 12, and 24 hours. After incubation the medium was replaced with normal culture medium for 24 hours. Bax expression was measured to assess the commitment to apoptosis.
Figure 7:
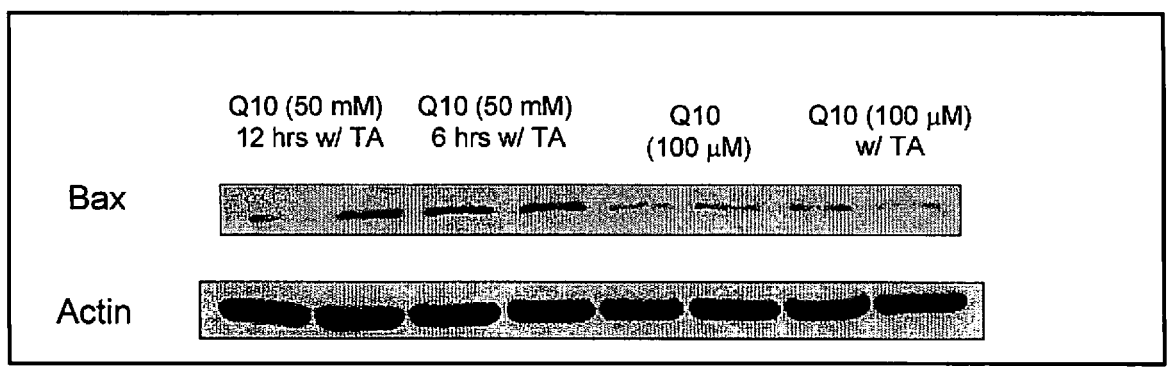
Figure 8:
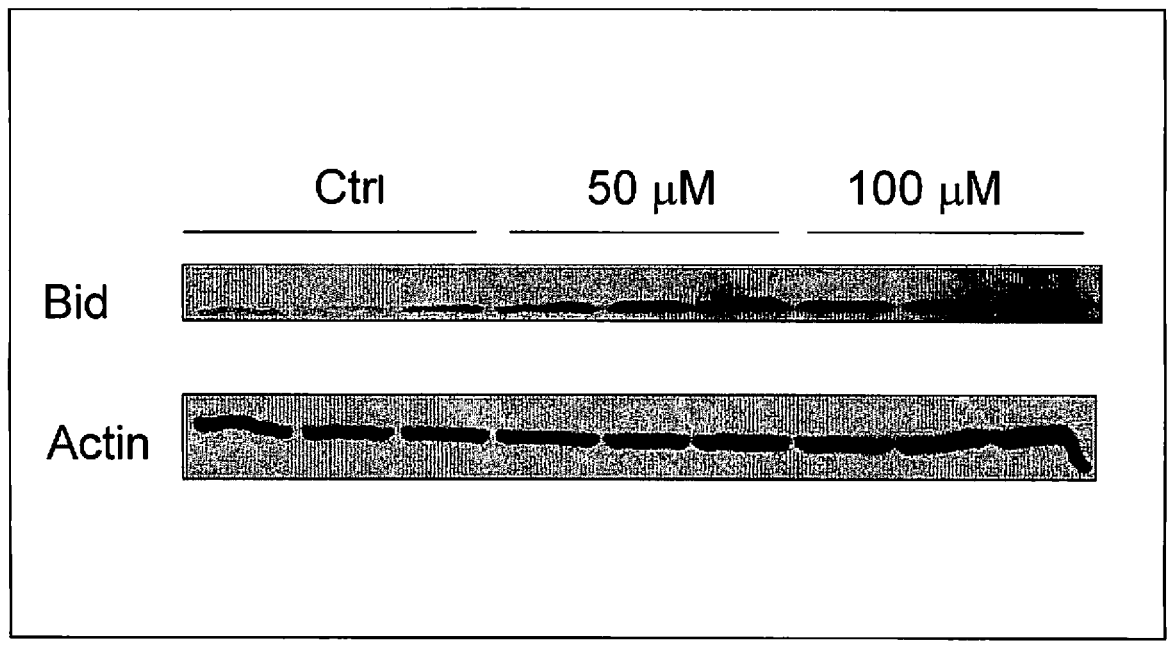
FIG. 8 shows Bid expression in melanoma cells after 12 hours incubation with CoQ10.
Figure 9:
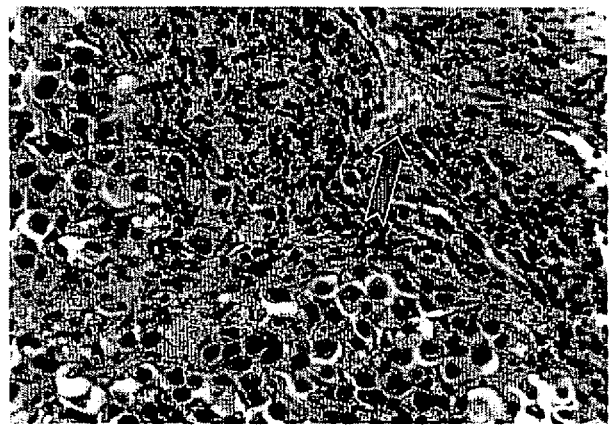
FIG. 9 shows the histopathology analysis of human melanoma tumors induced in nude athymic mice. The treatment group received a topical application of CoQ10 for 30 days. Analysis of the tumor pathology indicates a disruption in tumor vasculature.
Figure 9:
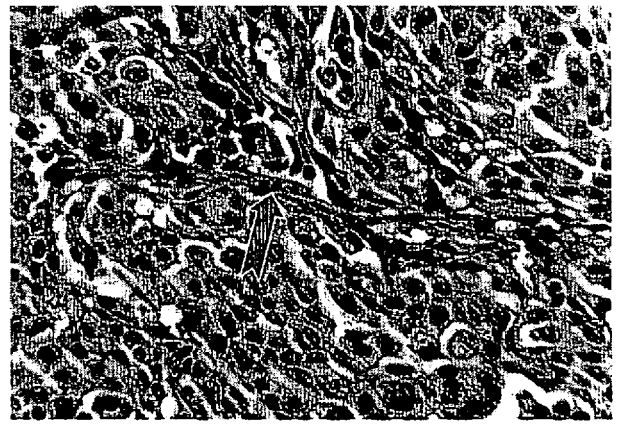
Figure 10A:
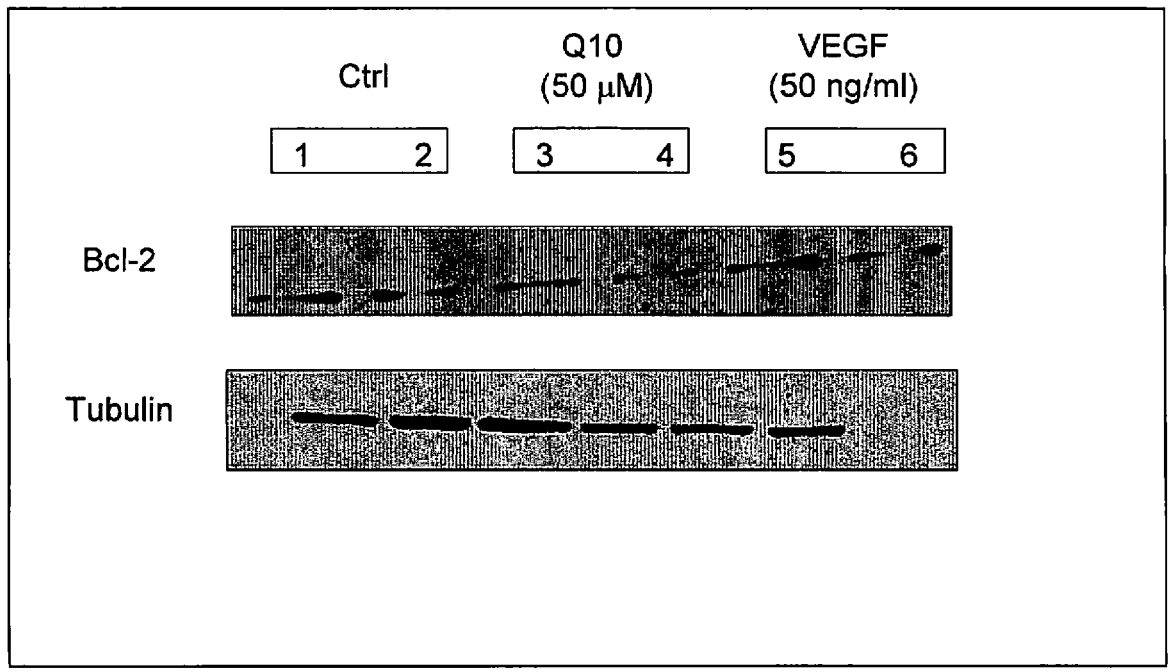
FIGS. 10a-10d show Bcl-2 expression in melanoma cells incubated with CoQ10 and/or Vascular Endothelial Growth Factor (VEGF) for 24 hours.
Figure 10B:
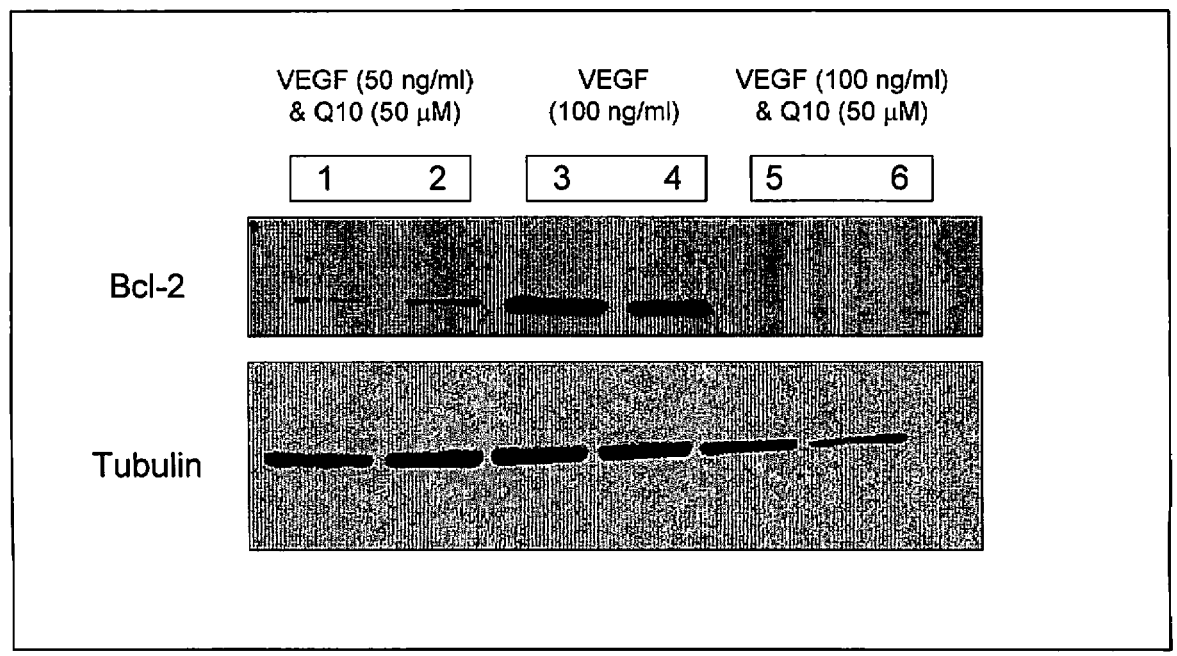
Figure 10C:
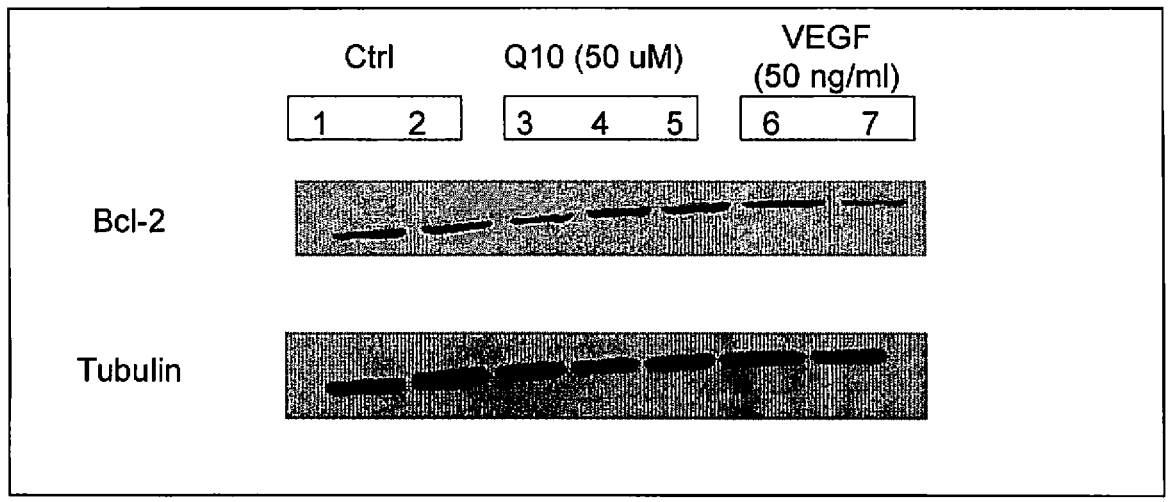
Figure 10D:
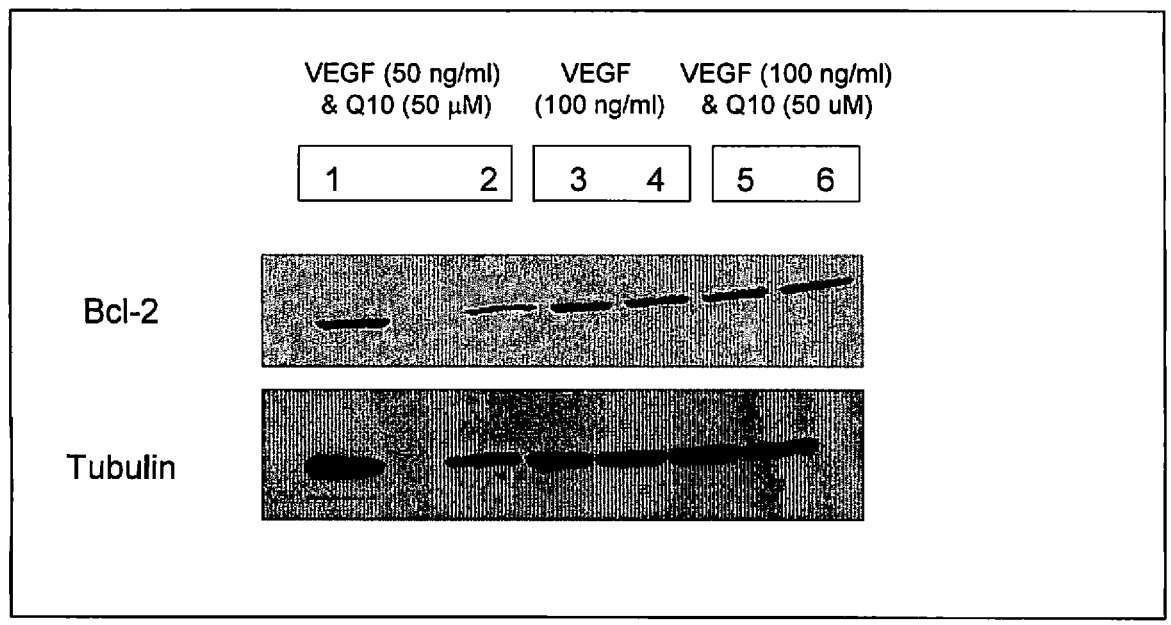
Figure 11:
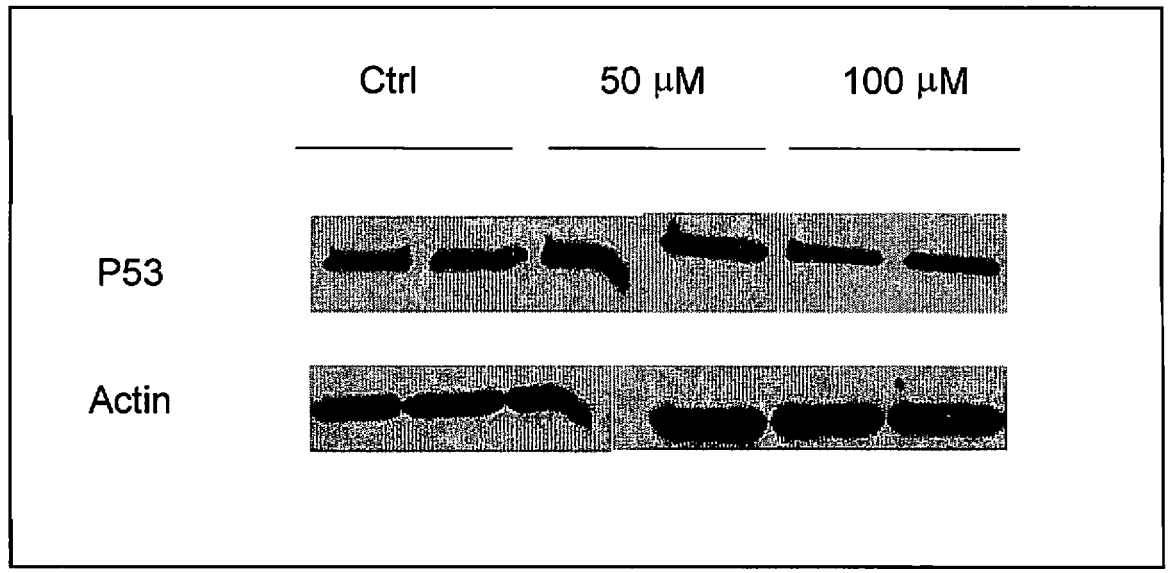
FIG. 11 shows p53 expression in melanoma cells incubated with 50 µM and 100 µM CoQ10 for 24 hours.
Figure 12:
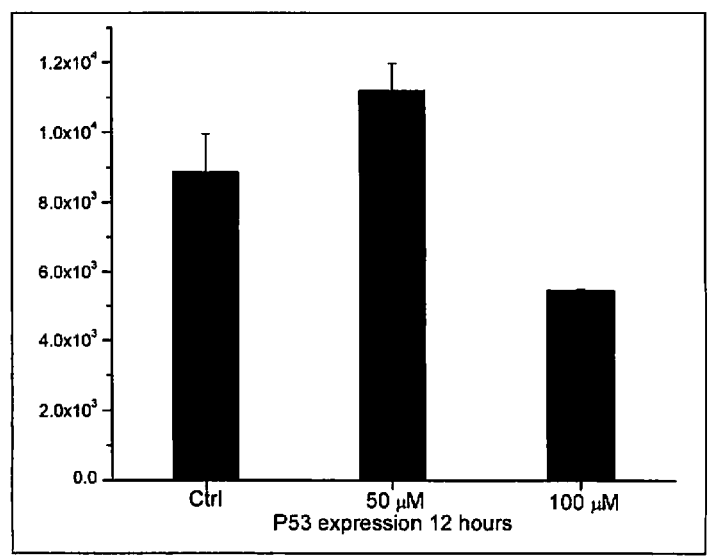
FIG. 12 is a graph depicting p53 expression in melanoma cells incubated with 50 µM and 100 µM CoQ10 for 12 hours.
Figure 13:
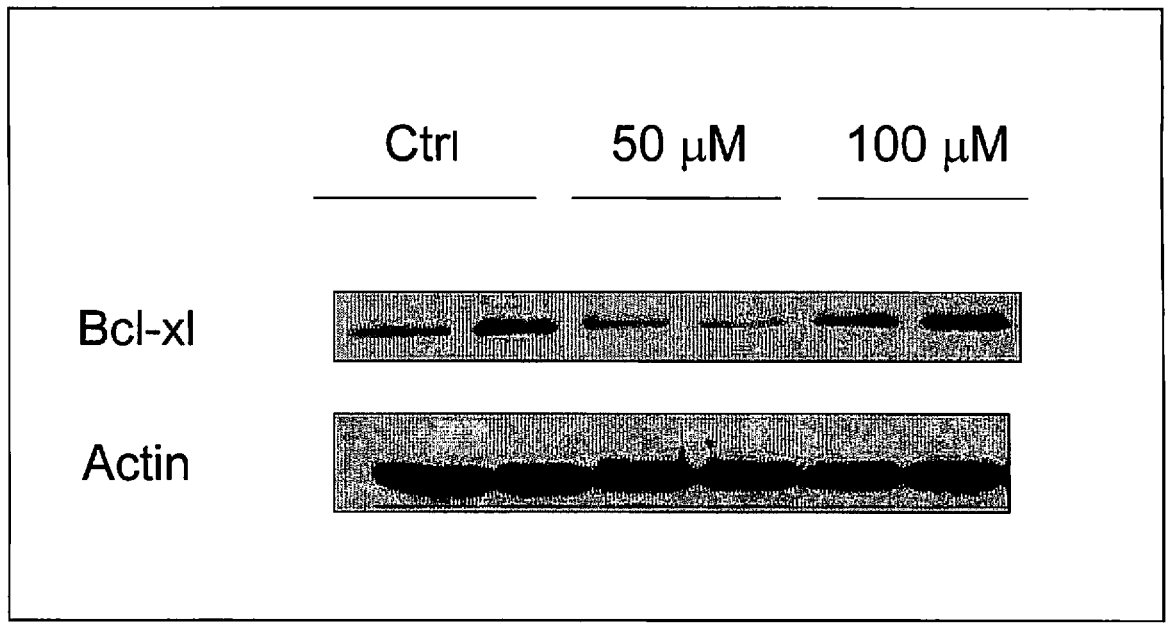
FIG. 13 shows Bcl-xl expression in melanoma cells incubated with CoQ10 for 6 hours.
Figure 14:
FIG. 14 shows Bcl-xl expression in melanoma cells incubated with CoQ10 for 12 hours.
Figure 15:
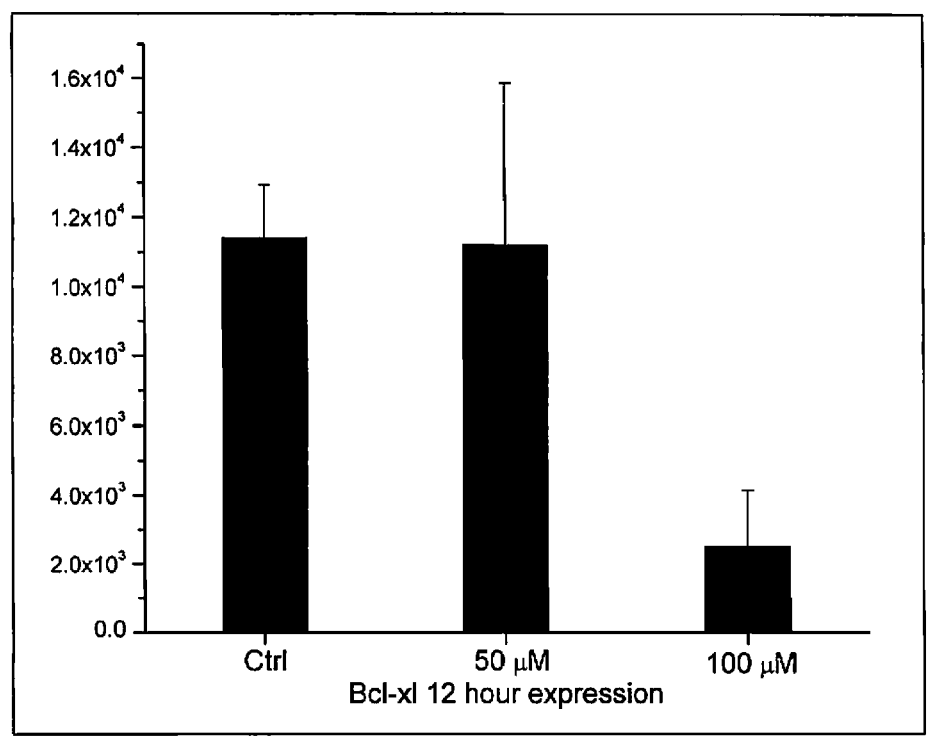
FIG. 15 is a graph quantifying Bcl-xl expression in melanoma cells treated for 12 hours with CoQ10.
Figure 16:
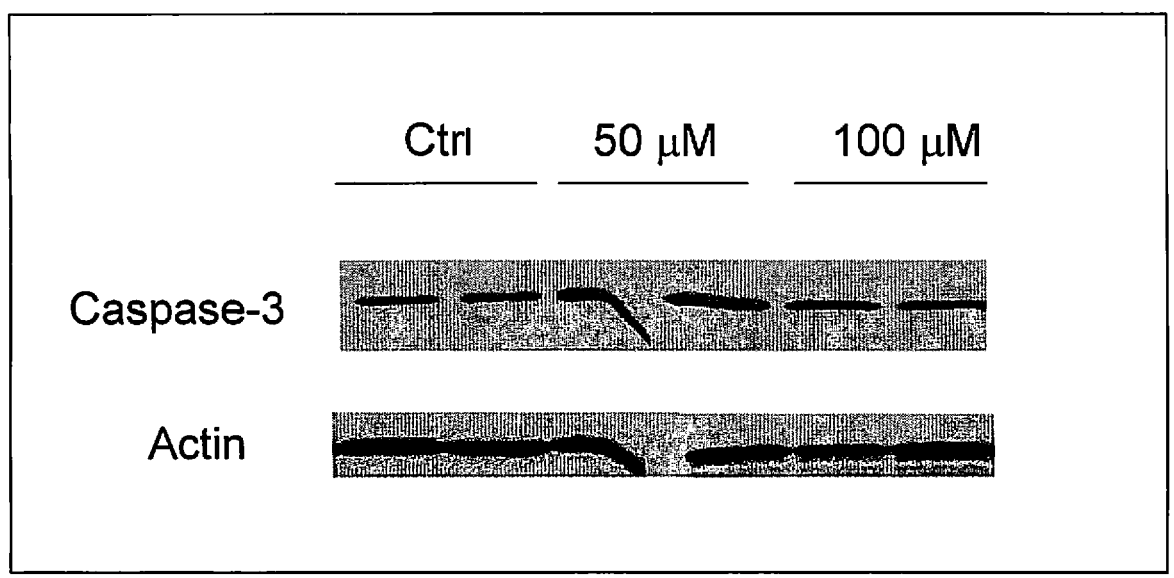
FIG. 16 shows Caspase-3 expression in melanoma cells treated for 12 hours with CoQ10.
Figure 17:
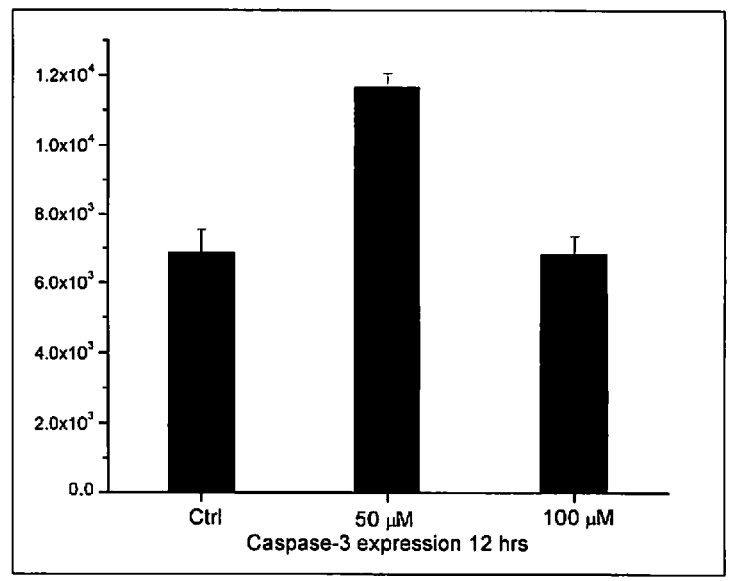
FIG. 17 is a graph quantifying Caspase-3 expression in melanoma cells treated for 12 hours with CoQ10.
Figure 18:
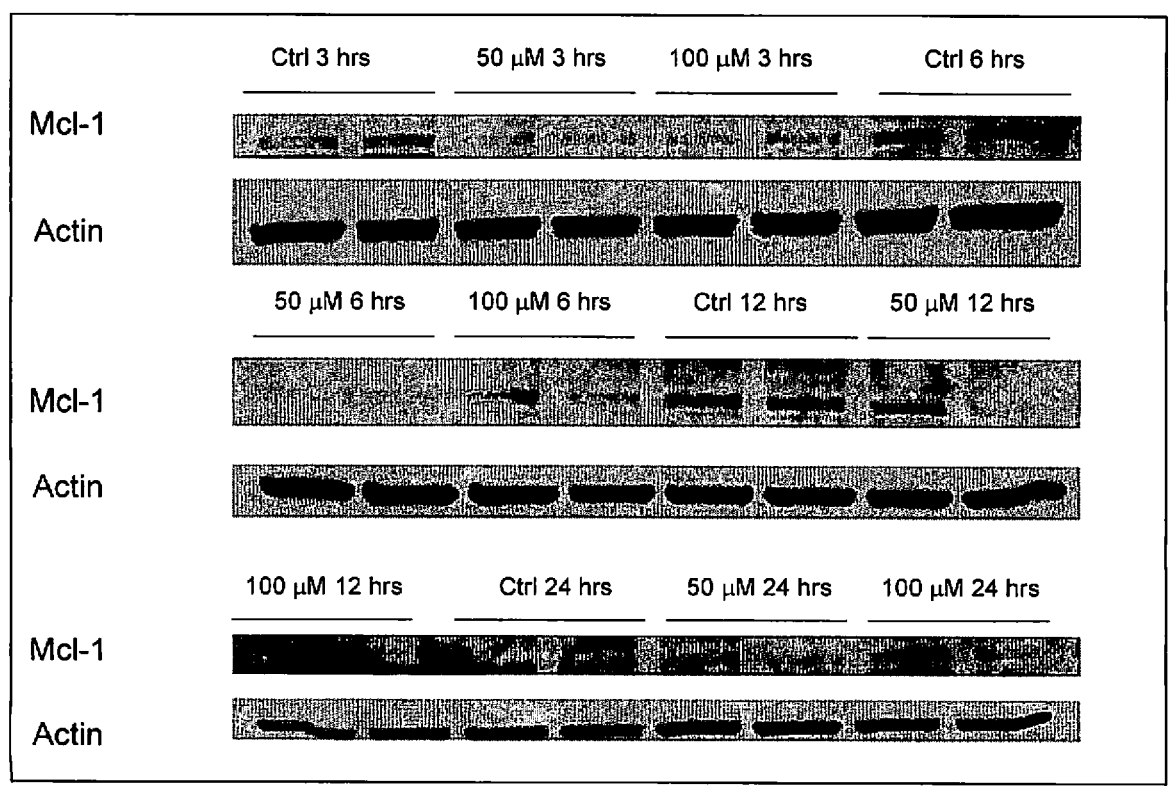
FIG. 18 shows Mcl-1 expression in melanoma cells treated with Coenzyme Q10 for 3, 6, 12, and 24 hours.
Figure 19A:
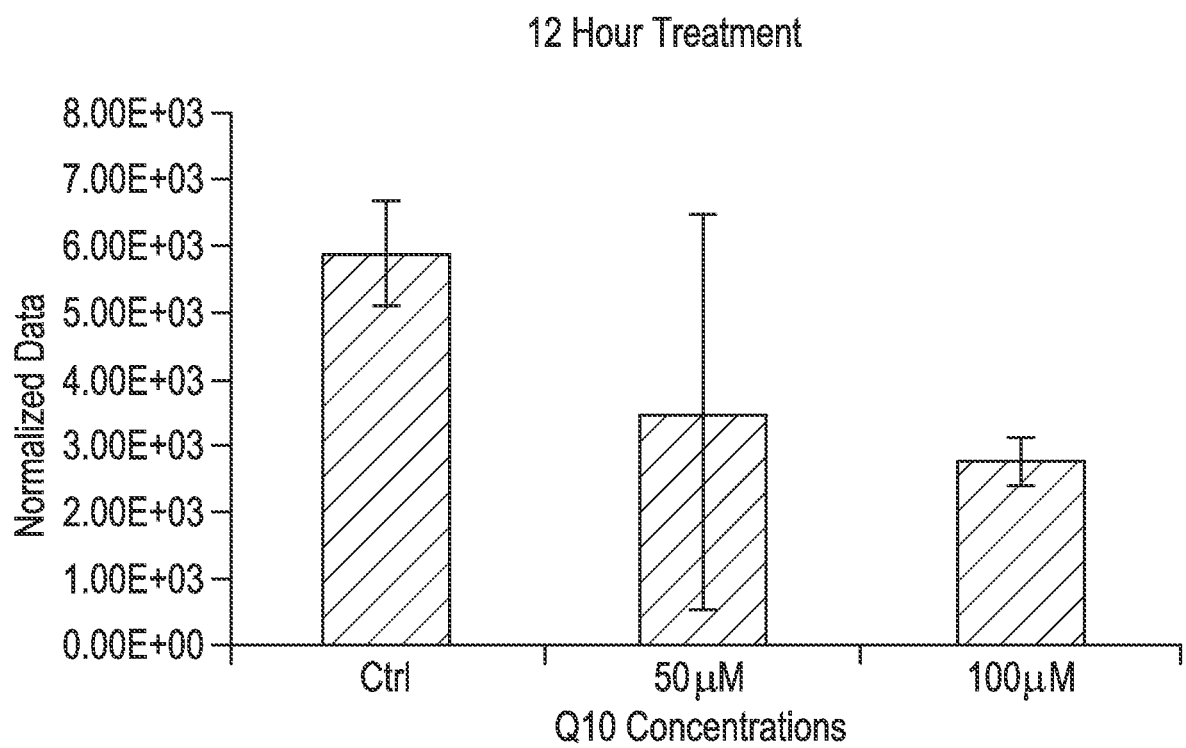
FIG. 19a is a graph quantifying Mcl-1 expression in melanoma cells incubated with CoQ10 for 12 hours.
Figure 19B:
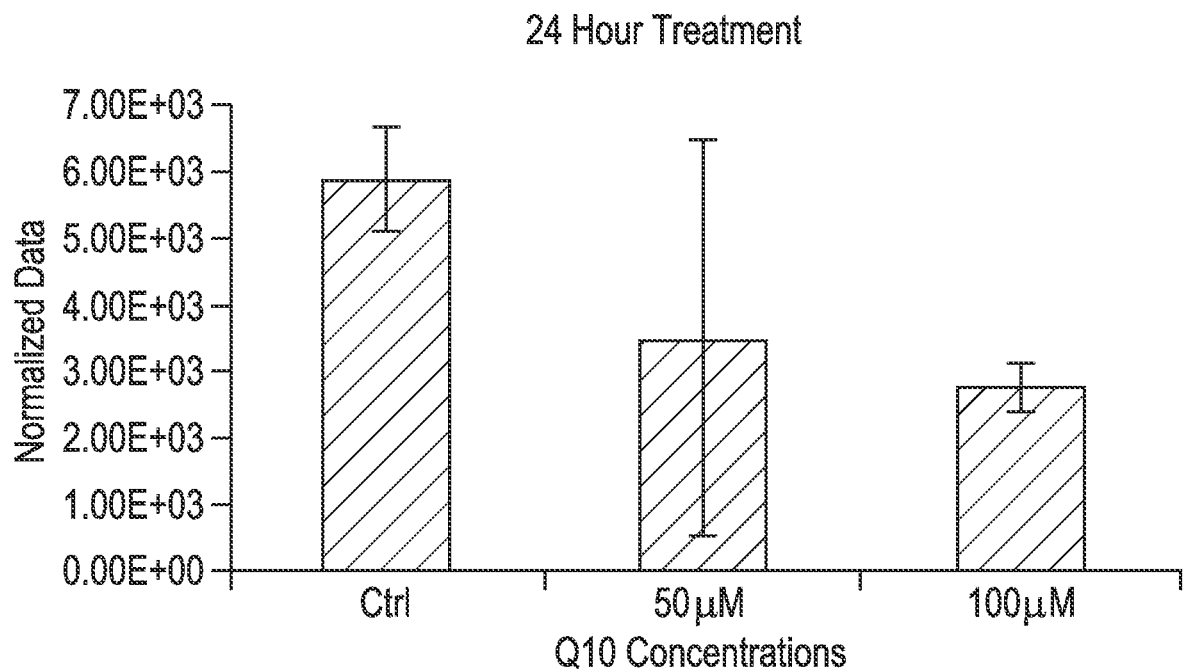
FIG. 19b is a graph quantifying Mcl-1 expression in melanoma cells incubated with CoQ10 for 24 hours.
Figure 20:
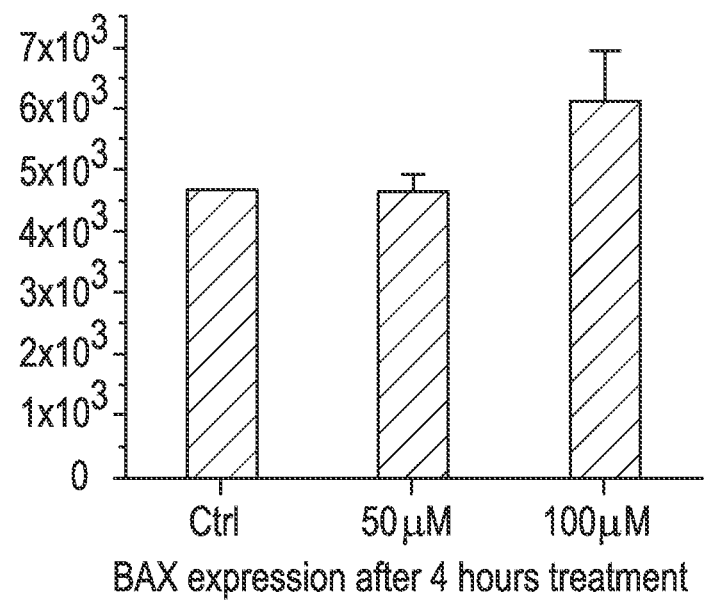
FIG. 20 is a graph quantifying BAX expression in PC-3 (prostate cancer) cells incubated for 4 hours with CoQ10.
Figure 21:
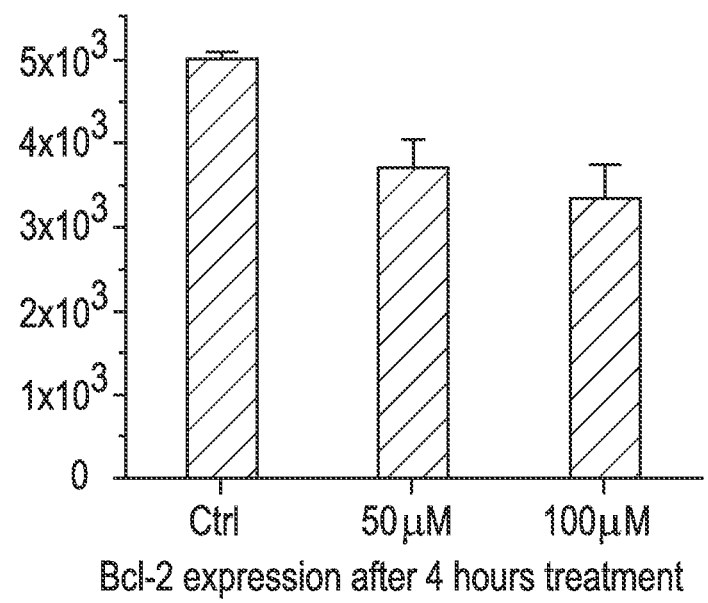
FIG. 21 is a graph quantifying Bcl-2 expression in PC-3 cells incubated for 4 hours with CoQ10.
Figure 22:
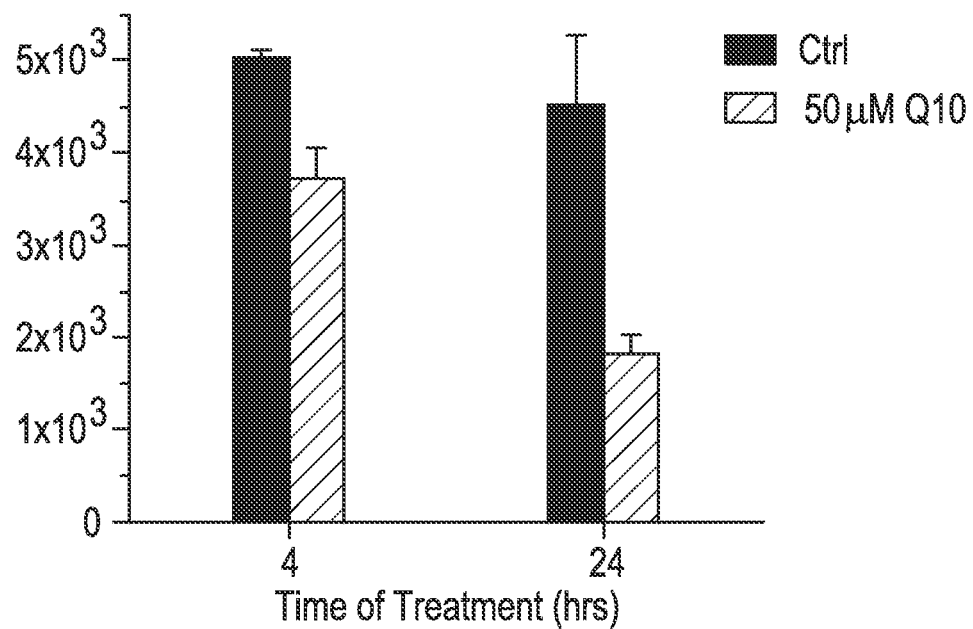
FIG. 22 is a graph showing the time point comparison of Bcl-2 expression in PC-3 cells treated with CoQ10 for 4 and 24 hours.
Figure 23:
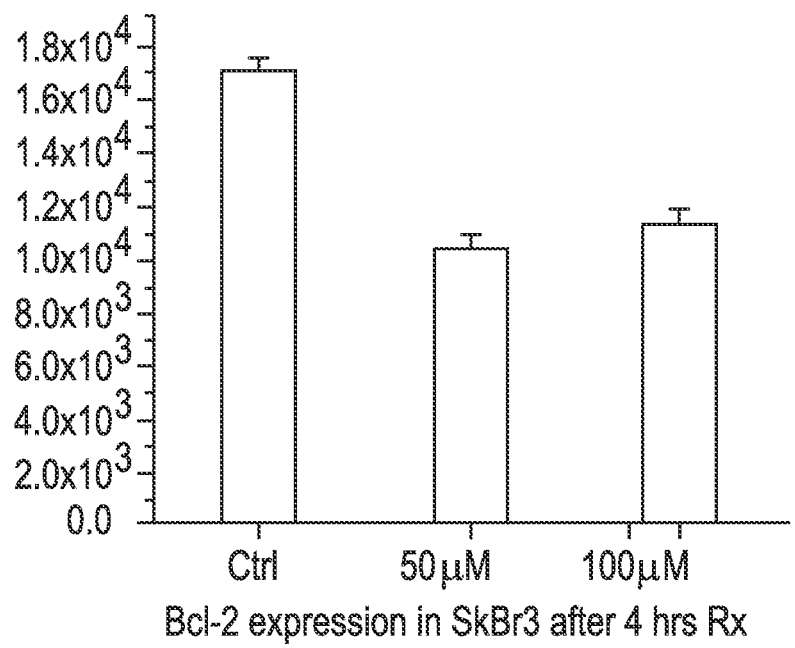
FIG. 23 is a graph quantifying Bcl-2 expression in SkBr-3 (breast cancer) cells incubated for 4 hours with CoQ10.
Figure 24:
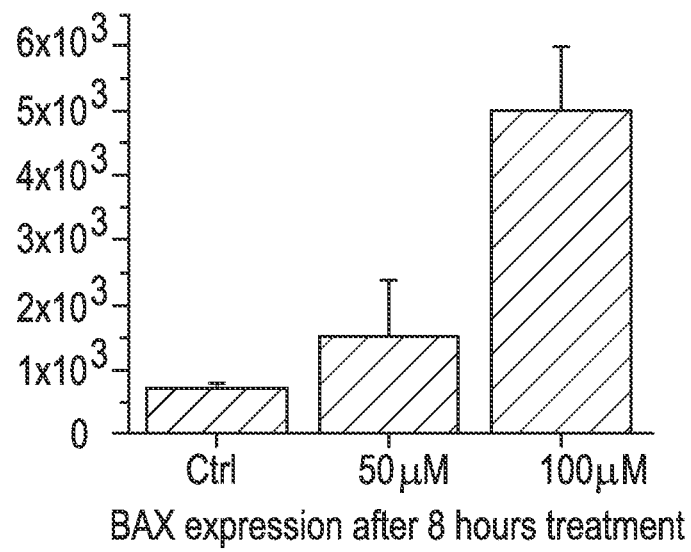
FIG. 24 is a graph quantifying Bax expression in SkBr-3 cells incubated for 8 hours with CoQ10.
Figure 25:
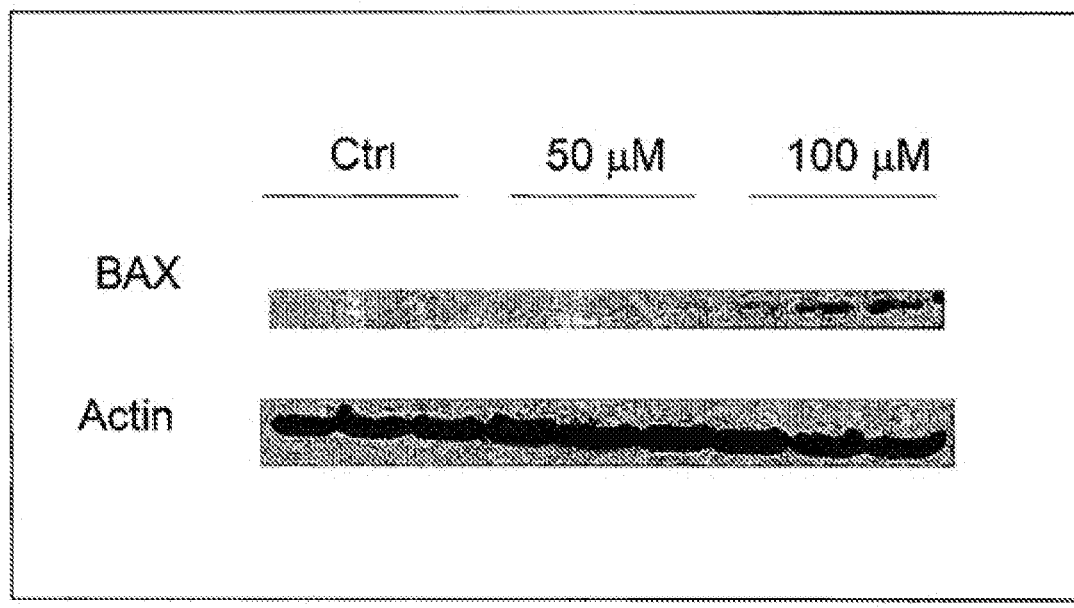
FIG. 25 shows Bax expression in SkBr3 cells incubated with CoQ10 for 8 hours.
Figure 26:
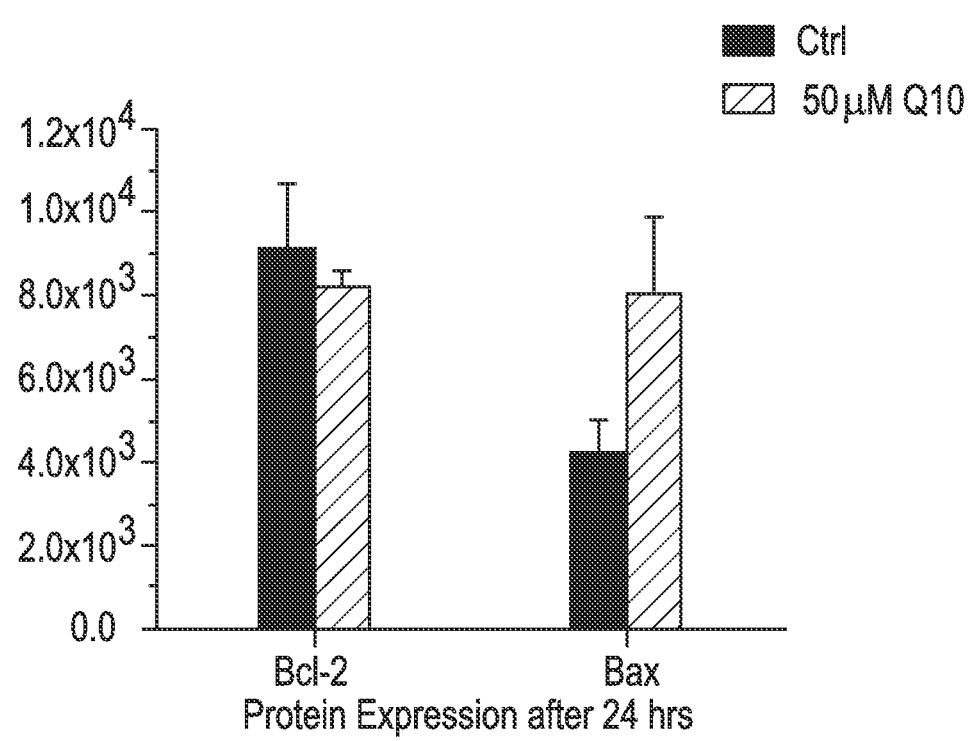
FIG. 26 is a graph comparing Bcl-2 and Bax expression after 24 hours treatment with CoQ10.

The Figures provide details regarding the synthesis of CoQ10, and the interactions of endogenous proteins in a cancer state, including their expression in cancer states. The Figures also depict the data obtained from the above experiments, and demonstrate the effects the administration of a compound such as CoQ10, in varying concentrations and for varying periods of time had on various types of cancer cells. Briefly, in summary, the Figures include the following:

FIG. 1 is a depiction of the metabolic synthesis of CoQ10;

FIG. 2 is a summary of the interactions of Bax, P53, and Bcl-2 in the induction of apoptosis;

FIG. 3 shows Bcl-2 expression in melanoma cells and neonatal fibroblasts after treatment with 50 μM CoQ10;

FIG. 4 shows Bcl-2 expression in melanoma cells incubated with 50 μM and 100 μM CoQ10 for 24 hours;

FIG. 5 shows Bcl-2 expression in melanoma cells treated in the presence and absence of CoQ10 using a 24 hour Take Away (TA) method. In TA experiments, melanoma cells were treated with CoQ10 for 6, 12, and 24 hours. After incubation the medium was replaced with normal culture medium for 24 hours. Bcl-2 expression was measured to assess the commitment to apoptosis;

FIG. 6 shows Bax expression in melanoma cells after 12 and 24 hours incubation with CoQ10 (50 μM and 100 μM);

FIG. 7 shows fax expression in melanoma cells treated in the presence and absence of CoQ10 using 24 hr Take Away (TA) method. In TA experiments melanoma cells were treated with CoQ10 for 6, 12, and 24 hours. After incubation the medium was replaced with normal culture medium for 24 hours. Bax expression was measured to assess the commitment to apoptosis;

FIG. 8 shows Bid expression in melanoma cells after 12 hours incubation with CoQ10;

FIG. 9 shows the histopathology analysis of human melanoma tumors induced in nude athymic mice. The treatment group received a topical application of CoQ10 for 30 days. Analysis of the tumor pathology indicates a disruption in tumor vasculature;

FIGS. 10a-10d show Bcl-2 expression in melanoma cells incubated with CoQ10 and/or Vascular Endothelial Growth Factor (VEGF) for 24 hours;

FIG. 11 shows p53 expression in melanoma cells incubated with 50 μM and 100 μM CoQ10 for 24 hours;

FIG. 12 is a graph depicting p53 expression in melanoma cells incubated with 50 μM and 100 μM CoQ10 for 12 hours;

FIG. 13 shows Bcl-xl expression in melanoma cells incubated with CoQ10 for 6 hours;

FIG. 14 shows Bcl-xl expression in melanoma cells incubated with CoQ10 for 12 hours;

FIG. 15 is a graph quantifying Bcl-xl expression in melanoma cells treated for 12 hours with CoQ10;

FIG. 16 shows Caspase-3 expression in melanoma cells treated for 12 hours with CoQ10;

FIG. 17 is a graph quantifying Caspase-3 expression in melanoma cells treated for 12 hours with CoQ10;

FIG. 18 shows Mcl-1 expression in melanoma cells treated with Coenzyme Q10 for 3, 6, 12, and 24 hours;

FIG. 19a is a graph quantifying Mcl-1 expression in melanoma cells incubated with CoQ10 for 12 hours; FIG. 19b is a graph quantifying Mcl-1 expression in melanoma cells incubated with CoQ10 for 24 hours;

FIG. 20 is a graph quantifying BAX expression in PC-3 (prostate cancer) cells incubated for 4 hours with CoQ10;

FIG. 21 is a graph quantifying Bcl-2 expression in PC-3 cells incubated for 4 hours with CoQ10;

FIG. 22 is a graph showing the time point comparison of Bcl-2 expression in PC-3 cells treated with CoQ10 for 4 and 24 hours;

FIG. 23 is a graph quantifying Bcl-2 expression in SkBr-3 (breast cancer) cells incubated for 4 hours with CoQ10;

FIG. 24 is a graph quantifying Bax expression in SkBr-3 cells incubated for 8 hours with CoQ10;

FIG. 25 shows Bax expression in SkBr3 cells incubated with CoQ10 for 8 hours;

FIG. 26 is a graph comparing Bcl-2 and Bax expression after 24 hours treatment with CoQ10.

Conditions/Disorders/Uses

As noted above, compositions of the present disclosure may be utilized for the treatment of cancer. Such compositions may include CoQ10 or its metabolites in a pharmaceutically acceptable carrier. Such a composition may effectuate cell contact of endogenous Coenzyme Q10 or its metabolites thereof in addition to, but not limited to, mevalonic acid and oleic acid to form an intracellular complex. In embodiments, such a composition may include from about 0.001% to about 60% (w/w) of Coenzyme Q10. Such compositions may be topical compositions which, in turn, may be gels, ointments, liquids, creams, salves, lotions, sprays, aerosols, mousses, foams, combinations thereof, and the like.

As also noted above, compositions of the present disclosure may be in a liquid form, capable of introduction into a subject by any means or route of administration within the purview of those skilled in the art. For example, compositions may be administered by routes of administration including, but not limited to, the lungs, intravenous, oral, transdermal, rectal, subcutaneous, transmucosal, buccal, sublingual, intratumoral, combinations thereof, and the like.

In some embodiments, it may be desirable to nebulize or aerosolize the compositions for administration.

Methods for treating disease states with the compositions herein are also provided. Such methods may include treating cancer. Where utilized to treat cancer, the compositions may be in a pharmaceutically acceptable carrier that may be administered in a therapeutically effective amount to an area of oncogenesis as either a monotherapy, in combination with at least one other chemotherapeutic agent for a given indication, in combination with radiotherapy, following surgical intervention to radically remove a tumor, in combination with other alternative and/or complementary acceptable treatments for cancer, and the like.

In embodiments, the present disclosure also provides a method claim for re-activating a mutated/inactivated p53 protein by administering to an area of oncogenesis in a patient a composition of the present disclosure.

The present disclosure also provides methods for modulating proteins implicated in oncogenesis by administering to an area of oncogenesis in a patient a composition of the present disclosure. Such proteins which may be modulated by compositions of the present disclosure include, but are not limited to Bcl-2 protein; Bax protein; Bid protein; Bim protein; Bad protein; Bak protein; mcl-1 protein; Bcl-xl protein; Bcl-xs protein; Bcl-w protein; Bik protein; Bok protein; BimL protein; A1 protein; Hrk protein; Bik protein; BNIP3 protein; Blk protein; Noxa protein; Puma protein; VEGF protein; FGF-1/FGF-2 protein; Hif-α protein; angiostatin protein; TGF-β protein; smad proteins; cdk (cyclin-dependent kinases); the PI3K/akt complex.

In other embodiments, compositions of the present disclosure may be utilized to regulate and/or restore a healthy apoptosis state in cancer cells. Mitochondrial dysfunction and dysregulation of apoptosis are implicated in many diseases such as cancer and neurodegeneration. Respiratory chain (RC) dysfunction may have a role in apoptosis, as demonstrated using mitochondrial DNA mutations as genetic models. Although some mutations eliminate the entire RC, others target specific complexes, resulting in either decreased or complete loss of electron flux, which leads to impaired respiration and adenosine triphosphate (ATP) synthesis. Despite these similarities, significant differences in responses to apoptotic stimuli emerge. Cells lacking RC are protected against both mitochondrial- and endoplasmic reticulum (ER) stress-induced apoptosis. Cells with RC, but unable to generate electron flux, are protected against mitochondrial apoptosis, although they have increased sensitivity to ER stress. Finally, cells with a partial reduction in electron flux have increased apoptosis under both conditions. RC modulates apoptosis in a context-dependent manner independent of ATP production and that apoptotic responses are the result of the interplay between mitochondrial functional state and environmental cues.

The execution of apoptosis and communication between oncogenic factors may also be mediated by released factors such as cytochrome C, Endo G, or AIF through mitochondrial membrane pores which open upon membrane depolarization.

Cancer cells also generate excessive lactate in the presence of oxygen (aerobic glycolysis). It now appears that this phenomenon is the product of two factors: a return to the more glycolytic metabolism of the embryo and alterations in oxidative phosphorylation (OXPHOS) to increase mitochondrial reactive oxygen species (ROS) production. Alterations in the Ras-PI3K-Akt signal transduction pathway can result in induction of hexokinase II and its attachment to mitochondrial porin redirecting mitochondrial ATP to phosphorylate glucose and drive glycolysis. Furthermore, partial inhibition of OXPHOS by mitochondrial gene mutations (germ-line or somatic) can reduce electron flux through the electron transport chain, increasing mitochondrial ROS production. The increased ROS mutagenizes nuclear proto-oncogenes (initiation) and drives nuclear replication (promotion), resulting in cancer. Therefore, hexokinase II and mitochondrial ROS may be useful alternate targets for cancer therapeutics.

Metabolic flux as it relates to cancer is compromised in an oncogenic state and shifts towards a glycolytic state. A cancer cell's survival is vitally dependent on glucose metabolism and low oxygen levels. More perplexing is that mitochondrial activity is significantly attenuated to the point of dormancy. Oxidative phosphorylation usually associated with Complex I-IV that accepts electrons from the Citric Acid Cycle (TCA) is essentially shut down. There is a marked increase in the amount of free radicals and lactate dehydrogenase activity. Hence, the cancer cell is in state of:
  1) Decreased oxygen (Hypoxia)
  2) Increase free-radical formation
  3) Dysregulated apoptosis (cell death)
  4) Dependence of glucose metabolism
  5) Increased blood vessel formation
  6) Altered immune recognition (auto-regulatory state commences)

In embodiments, the effect CoQ10 may have on cancer cells may depend, in part, on the various states of metabolic and oxidative flux exhibited by the cancer cells. CoQ10 may be utilized to interrupt and/or interfere with the conversion of an oncogenic cell's dependency of glycolysis and increased lactate utility. As it relates to a cancer state, this interference with the glycolytic and oxidative flux of the tumor microenvironment may influence apoptosis and angiogenesis in a manner which reduces the development of a cancer cell.

In embodiments, the interaction of Coenzyme Q10 with glycolytic and oxidative flux factors may enhance the ability of Coenzyme Q10 to exert its restorative apoptotic effect in cancer while establishing viable drug targets for drug discovery and development.

While the above disclosure has focused on Coenzyme Q10 and its metabolites, other compounds related to CoQ10 which may be administered instead of, or in combination with, CoQ10 include, but are not limited to, benzoquinones, isoprenoids, farnesols, farnesyl acetate, farnesyl pyrophosphate, 1-phenylalanine, d-phenylalanine, dl-phenylalanine, l-tyrosine, d-tyrosine, dl-tyrosine, 4-hydroxy-phenylpyruvate, 4-hydroxy-phenyllactate, 4-hydroxy-cinnamate, dipeptides and tripeptides of tyrosine or phenylalanine, 3,4-dihydroxymandelate, 3-methoxy-4-hydroxyphenylglycol, 3-methoxy-4-hydroxymandelate, vanillic acid, phenylacetate, pyridoxine, S-adenosyl methionine, panthenol, mevalonic acid, isopentyl pyrophosphate, phenylbutyrate, 4-hydroxy-benzoate, decaprenyl pyrophosphate, beta-hydroxybutyrate, 3-hydroxy-3-methyl-glutarate, acetylcarnitine, acetoacetylcarnitine, acetylglycine, acetoacetylglycine, carnitine, acetic acid, pyruvic acid, 3-hydroxy-3-methylglutarylcarnitine, all isomeric forms of serine, alanine, cysteine, glycine, threonine, hydroxyproline, lysine, isoleucine, and leucine, even carbon number C4 to C18 fatty acids (butyric, caproic, caprylic, capric, lauric, myristic, palmitic, and stearic acids) salts of carnitine and glycine, e.g., palmitoylcarnitine and palmitoylglycine, and 4-hydroxy-benzoate polyprenyltransferase, any salts of these compounds, as well as any combinations thereof, and the like.

The figures are offered by way of illustration, not by way of limitation. While specific examples have been provided, the above description is illustrative and not restrictive. Any one or more of the features of the previously described embodiments can be combined in any manner with one or more features of any other embodiments in the present disclosure. Furthermore, many variations of the present disclosure will become apparent to those skilled in the art upon review of the specification.

Other References

All publications and patent documents cited in this application are incorporated by reference in pertinent part for all purposes to the same extent as if each individual publication or patent document were so individually denoted. By their citation of various references in this document. Applicants do not admit any particular reference is "prior art" to their disclosure.

It is to be understood that while the present disclosure has been described in conjunction with the detailed description thereof, the foregoing description is intended to illustrate and not limit the scope of the present disclosure, which is defined by the scope of the appended claims. Other aspects, advantages, and modifications are within the scope of the following claims and their equivalents.

What is claimed is:
1. A method for normalizing protein expression level of the oncogenic markers Bcl-2, Bax and caspase 3 in a patient with cancer, the method comprising:
   (a) administering to the patient a composition comprising a therapeutically effective dose of Coenzyme Q10; and

(b) detecting a protein expression level of the oncogenic markers Bcl-2, Bax and caspase 3 in a tumor sample obtained from the patient after administration of Coenzyme Q10 that is less than 50% different from a normalized oncogenic marker protein expression level, wherein the normalizing of the protein expression level of the oncogenic markers is achieved by administering the composition comprising a therapeutically effective dose of Coenzyme Q10 to the patient.

2. The method of claim 1, wherein the protein expression level of the oncogenic markers detected in the tumor sample is less than 25% different from a normalized oncogenic marker protein expression level.

3. The method of claim 1, wherein the protein expression level of at least one of the oncogenic markers detected in the tumor sample is less than 10% different from a normalized oncogenic marker protein expression level.

4. The method of claim 1, further comprising detecting a protein expression level of at least one additional oncogenic marker selected from the group consisting of Bid, Mcl-1, and Bcl-xl in a tumor sample from the patient after administration of the Coenzyme Q10.

* * * * *